United States Patent
Levi et al.

(10) Patent No.: US 9,393,110 B2
(45) Date of Patent: Jul. 19, 2016

(54) PROSTHETIC HEART VALVE

(75) Inventors: Tamir S. Levi, Moshav Ein HaEmek (IL); Son V. Nguyen, Irvine, CA (US); Netanel Benichou, D.N. Hof HaCarmel (IL); David Maimon, Haifa (IL); Ziv Yohanan, Yesud Hamaala (IL); Nikolay Gurovich, Hadera (IL); Bella Felsen, Haifa (IL); Larisa Dadonkina, Or Akiva (IL); Ron Sharoni, Hadera (IL); Elena Sherman, Ramat Hasharon (IL)

(73) Assignee: Edwards Lifesciences Corporation, Irvine, CA (US)

( * ) Notice: Subject to any disclaimer, the term of this patent is extended or adjusted under 35 U.S.C. 154(b) by 844 days.

(21) Appl. No.: 13/253,689

(22) Filed: Oct. 5, 2011

(65) Prior Publication Data

US 2012/0123529 A1     May 17, 2012

Related U.S. Application Data

(60) Provisional application No. 61/390,107, filed on Oct. 5, 2010, provisional application No. 61/508,513, filed on Jul. 15, 2011.

(51) Int. Cl.
*A61F 2/24*     (2006.01)

(52) U.S. Cl.
CPC .............. *A61F 2/2412* (2013.01); *A61F 2/2418* (2013.01); *A61F 2/2433* (2013.01);
(Continued)

(58) Field of Classification Search
CPC ....... A61F 2/24; A61F 2/2412; A61F 2/2418; A61F 2/2427; A61F 2/243; A61F 2/2433; A61F 2/2469; A61F 2220/0075; A61F 2250/0036; A61F 2250/0039

USPC ........... 623/2.11, 2.12, 2.17, 2.19, 1.11, 1.12, 623/1.24, 1.26
See application file for complete search history.

(56) References Cited

U.S. PATENT DOCUMENTS 3,409,013 A    11/1968   Berry
3,467,102 A     9/1969   Fogarty et al.
(Continued)

FOREIGN PATENT DOCUMENTS

DE    2246526 A1    3/1973
DE   19532846 A1    3/1997
(Continued)

OTHER PUBLICATIONS

International Search Report from corresponding PCT application No. PCT/US2011/054973 dated Apr. 23, 2012.
(Continued)

*Primary Examiner* — Todd J Scherbel
(74) *Attorney, Agent, or Firm* — Klarquist Sparkman LLP; David L. Hauser; AnneMarie Kaiser

(57) ABSTRACT

Embodiments of a radially collapsible and expandable prosthetic heart valve are disclosed. A valve frame can have a tapered profile when mounted on a delivery shaft, with an inflow end portion having a smaller diameter than an outflow end portion. The valve can comprise generally V-shaped leaflets, reducing material within the inflow end of the frame. An outer skirt can be secured to the outside of the inflow end portion of the frame, the outer skirt having longitudinal slack when the valve is expanded and lying flat against the frame when the valve is collapsed. A diagonally woven inner skirt can elongate axially with the frame. Side tabs of adjacent leaflets can extend through and be secured to window frame portions of the frame to form commissures. The window frame portions can be depressed radially inward relative to surrounding frame portions when the valve is crimped onto a delivery shaft.

25 Claims, 26 Drawing Sheets

(52) U.S. Cl.
CPC . *A61F2220/0075* (2013.01); *A61F 2230/0054* (2013.01); *A61F 2250/0036* (2013.01); *A61F 2250/0097* (2013.01)

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,983,581 A | 10/1976 | Angell et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,258,023 A | 11/1993 | Reger |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,628,786 A | 5/1997 | Banas et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,928,281 A | 7/1999 | Huynh et al. |
| 5,957,949 A | 9/1999 | Leonhardt et al. |
| 6,027,525 A | 2/2000 | Suh et al. |
| 6,110,198 A | 8/2000 | Fogarty et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,312,465 B1 | 11/2001 | Griffin et al. |
| 6,350,277 B1 | 2/2002 | Kocur |
| 6,352,554 B2 | 3/2002 | De Paulis |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,569,196 B1 | 5/2003 | Vesely |
| 6,605,112 B1 | 8/2003 | Moll et al. |
| 6,610,088 B1 | 8/2003 | Gabbay |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,814,754 B2 | 11/2004 | Greenhalgh |
| 6,830,584 B1 | 12/2004 | Seguin |
| 6,837,902 B2 | 1/2005 | Nguyen |
| 6,893,460 B2 | 5/2005 | Spenser et al. |
| 6,908,481 B2 | 6/2005 | Cribier |
| 6,911,040 B2 | 6/2005 | Johnson et al. |
| 7,018,406 B2 | 3/2006 | Seguin et al. |
| 7,101,396 B2 | 9/2006 | Artof |
| 7,147,663 B1 | 12/2006 | Berg et al. |
| 7,261,732 B2 | 8/2007 | Justino |
| 7,264,632 B2 | 9/2007 | Wright et al. |
| 7,267,686 B2 | 9/2007 | Dimatteo et al. |
| 7,276,078 B2 | 10/2007 | Spenser et al. |
| 7,276,084 B2 | 10/2007 | Yang et al. |
| 7,374,571 B2 | 5/2008 | Pease et al. |
| 7,393,360 B2 | 7/2008 | Spenser et al. |
| 7,399,315 B2 | 7/2008 | Iobbi |
| 7,462,191 B2 | 12/2008 | Spenser et al. |
| 7,481,838 B2 | 1/2009 | Carpentier et al. |

(56) References Cited

U.S. PATENT DOCUMENTS

| | | | |
|---|---|---|---|
| 7,510,575 B2 | 3/2009 | Spenser et al. | |
| 7,524,331 B2 | 4/2009 | Birdsall | |
| 7,597,711 B2 | 10/2009 | Drews et al. | |
| 7,780,725 B2 | 8/2010 | Haug et al. | |
| 7,871,435 B2 | 1/2011 | Carpentier et al. | |
| 7,914,569 B2 | 3/2011 | Nguyen et al. | |
| 7,951,197 B2 | 5/2011 | Lane et al. | |
| 7,959,674 B2 | 6/2011 | Shu et al. | |
| 7,967,857 B2 | 6/2011 | Lane | |
| 7,972,378 B2 | 7/2011 | Tabor et al. | |
| 8,083,793 B2 | 12/2011 | Lane et al. | |
| 8,226,710 B2 | 7/2012 | Nguyen et al. | |
| 8,348,995 B2 | 1/2013 | Tuval et al. | |
| 8,348,998 B2 * | 1/2013 | Pintor et al. | 623/2.11 |
| 8,349,000 B2 | 1/2013 | Schreck | |
| 8,425,593 B2 | 4/2013 | Braido et al. | |
| 8,454,685 B2 | 6/2013 | Hariton et al. | |
| 8,512,396 B2 | 8/2013 | Styrc | |
| 8,673,000 B2 | 3/2014 | Tabor et al. | |
| 8,747,460 B2 | 6/2014 | Tuval et al. | |
| 8,771,345 B2 | 7/2014 | Tuval et al. | |
| 8,808,356 B2 | 8/2014 | Braido et al. | |
| 8,845,721 B2 | 9/2014 | Braido et al. | |
| 8,992,608 B2 | 3/2015 | Haug et al. | |
| 2001/0021872 A1 | 9/2001 | Bailey et al. | |
| 2001/0027338 A1 | 10/2001 | Greenberg | |
| 2002/0032481 A1 | 3/2002 | Gabbay | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0114913 A1 | 6/2003 | Spenser et al. | |
| 2003/0212454 A1 | 11/2003 | Scott et al. | |
| 2003/0236568 A1 | 12/2003 | Hojeibane et al. | |
| 2004/0039436 A1 * | 2/2004 | Spenser et al. | 623/1.13 |
| 2004/0186565 A1 | 9/2004 | Schreck | |
| 2004/0260389 A1 | 12/2004 | Case et al. | |
| 2005/0075718 A1 | 4/2005 | Nguyen et al. | |
| 2005/0075725 A1 | 4/2005 | Rowe | |
| 2005/0234546 A1 | 10/2005 | Nugent et al. | |
| 2006/0025857 A1 | 2/2006 | Bergheim et al. | |
| 2006/0149350 A1 | 7/2006 | Patel et al. | |
| 2006/0178740 A1 | 8/2006 | Stacchino et al. | |
| 2006/0195186 A1 | 8/2006 | Drews et al. | |
| 2006/0229719 A1 | 10/2006 | Marquez et al. | |
| 2006/0259136 A1 * | 11/2006 | Nguyen et al. | 623/2.18 |
| 2006/0259137 A1 | 11/2006 | Artof et al. | |
| 2006/0265056 A1 | 11/2006 | Nguyen et al. | |
| 2007/0073387 A1 | 3/2007 | Forster | |
| 2007/0270944 A1 | 11/2007 | Bergheim et al. | |
| 2008/0021546 A1 | 1/2008 | Patz et al. | |
| 2008/0154355 A1 | 6/2008 | Benichou et al. | |
| 2008/0208327 A1 | 8/2008 | Rowe | |
| 2008/0243245 A1 | 10/2008 | Thambar et al. | |
| 2008/0243246 A1 | 10/2008 | Ryan et al. | |
| 2009/0264997 A1 | 10/2009 | Salahieh et al. | |
| 2009/0287296 A1 | 11/2009 | Manasse | |
| 2009/0287299 A1 * | 11/2009 | Tabor et al. | 623/1.26 |
| 2010/0082094 A1 * | 4/2010 | Quadri et al. | 623/1.26 |
| 2010/0100176 A1 | 4/2010 | Elizondo et al. | |
| 2010/0168839 A1 | 7/2010 | Braido et al. | |
| 2010/0185277 A1 * | 7/2010 | Braido et al. | 623/2.18 |
| 2010/0204781 A1 | 8/2010 | Alkhatib | |
| 2010/0262231 A1 | 10/2010 | Tuval et al. | |
| 2011/0022157 A1 * | 1/2011 | Essinger | A61F 2/2418 623/1.26 |
| 2011/0282439 A1 | 11/2011 | Thill et al. | |
| 2011/0319988 A1 | 12/2011 | Schankereli et al. | |
| 2012/0035719 A1 | 2/2012 | Forster et al. | |
| 2012/0046742 A1 | 2/2012 | Tuval et al. | |
| 2012/0078357 A1 | 3/2012 | Conklin | |
| 2012/0083878 A1 | 4/2012 | Sequin | |
| 2012/0179244 A1 | 7/2012 | Schankereli | |
| 2012/0215303 A1 | 8/2012 | Quadri | |
| 2012/0232646 A1 | 9/2012 | Agathos | |
| 2012/0277856 A1 | 11/2012 | Spenser et al. | |
| 2012/0296418 A1 | 11/2012 | Bonyuet | |
| 2012/0316642 A1 | 12/2012 | Yu et al. | |
| 2013/0018458 A1 | 1/2013 | Yohanan et al. | |
| 2013/0023984 A1 | 1/2013 | Conklin | |
| 2013/0150956 A1 | 6/2013 | Yohanan et al. | |
| 2013/0204359 A1 | 8/2013 | Thubrikar et al. | |
| 2013/0211508 A1 | 8/2013 | Lane et al. | |
| 2013/0218267 A1 | 8/2013 | Braido et al. | |
| 2013/0274870 A1 | 10/2013 | Lombardi et al. | |
| 2013/0338765 A1 | 12/2013 | Braido et al. | |
| 2014/0142694 A1 | 5/2014 | Tabor et al. | |
| 2014/0350663 A1 | 11/2014 | Braido et al. | |
| 2014/0350665 A1 | 11/2014 | Braido et al. | |
| 2014/0350667 A1 | 11/2014 | Braido et al. | |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 2254513 | 12/2010 |
| EP | 2620125 | 7/2013 |
| EP | 2749254 | 7/2014 |
| FR | 2788217 A1 | 7/2000 |
| GB | 2056023 A | 3/1981 |
| JP | 2008541865 A | 11/2008 |
| JP | 2011500241 A | 1/2011 |
| JP | 2011522634 A | 8/2011 |
| JP | 2011528256 A | 11/2011 |
| JP | 2012504031 A | 2/2012 |
| SU | 158988 | 11/1963 |
| SU | 1271508 A1 | 11/1986 |
| SU | 1371700 A1 | 2/1988 |
| SU | 1457921 A1 | 2/1989 |
| WO | 91/17720 A1 | 11/1991 |
| WO | 92/17118 A1 | 10/1992 |
| WO | 93/01768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/35878 A2 | 5/2001 |
| WO | 01/49213 A2 | 7/2001 |
| WO | 01/54624 A1 | 8/2001 |
| WO | 01/54625 A1 | 8/2001 |
| WO | 01/62189 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 2005/087140 A1 | 9/2005 |
| WO | 2006/014233 A2 | 2/2006 |
| WO | 2006/034008 A2 | 3/2006 |
| WO | 2008/005405 A2 | 1/2008 |
| WO | 2008/035337 A2 | 3/2008 |
| WO | 2008/147964 A1 | 12/2008 |
| WO | 2008/150529 A1 | 12/2008 |
| WO | 2009042196 A2 | 4/2009 |

(56) References Cited

FOREIGN PATENT DOCUMENTS

| WO | 2009053497 A1 | | 4/2009 |
|---|---|---|---|
| WO | WO2009042196 | * | 4/2009 |
| WO | 2009/061389 A2 | | 5/2009 |
| WO | 2009149462 A2 | | 12/2009 |
| WO | 2010008548 A2 | | 1/2010 |
| WO | 2010037141 A1 | | 4/2010 |
| WO | WO2010/141847 | | 12/2010 |
| WO | 2012032187 A1 | | 3/2012 |
| WO | WO 2012/032187 | | 3/2012 |
| WO | WO 2012/161786 | | 11/2012 |

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Urban, M.D., Philip, "Coronary Artery Stenting," Editions Médecine et Hygiène, Genève, 1991, pp. 5-47.

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Al Zaibag, Muayed, et al., "Percutaneous Balloon Valvotomy in Tricuspid Stenosis," British Heart Journal, Jan. 1987, vol. 57, No. 1, pp. 51-53.

Lawrence, Jr., M.D., David D., "Percutaneous Endovascular Graft: Experimental Evaluation," Radiology 1897; 163: 357-360.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Ross, F.R.C.S., D.N., "Aortic Valve Surgery," Guy's Hospital, London, pp. 192-197, approximately 1968.

Rashkind, M.D., William J., "Creation of an Atrial Septal Defect Withoput Thoracotomy," the Journal of the American Medical Association, vol. 196, No. 11, Jun. 13, 1966, pp. 173-174.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Curriculum Vitae of Robert A. Ersek, M.D., FACS, Jul. 10, 2009, http://www.ersek.com/rae-cv.htm.

* cited by examiner

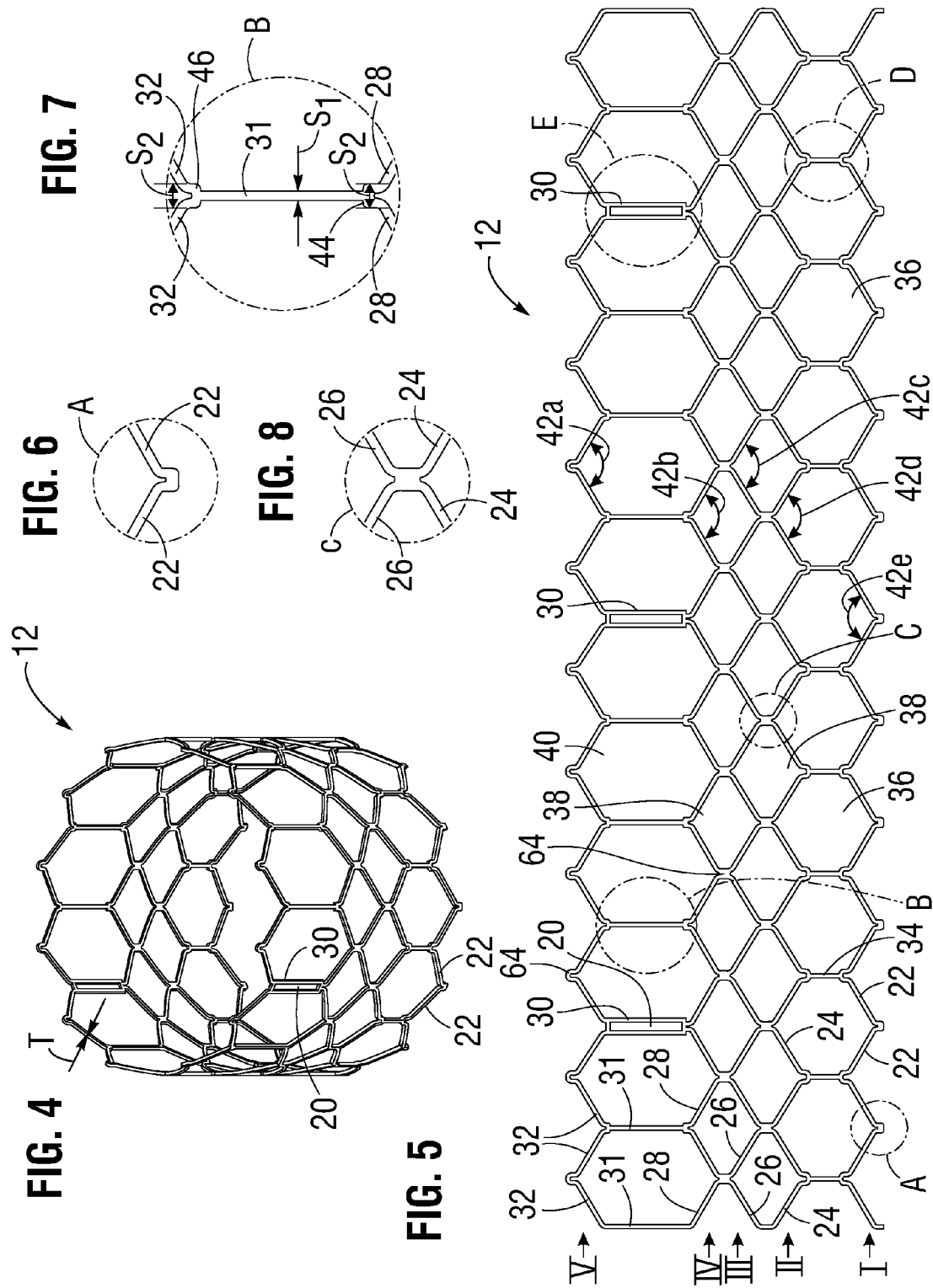

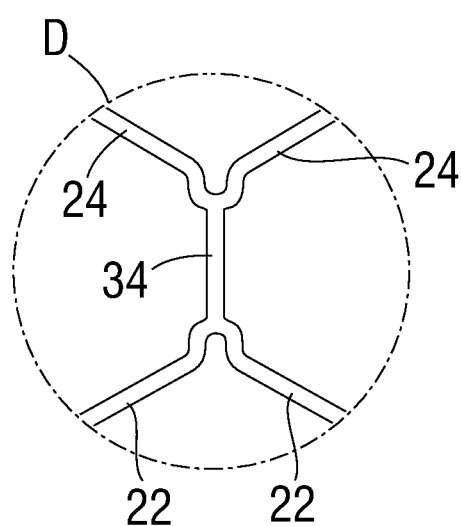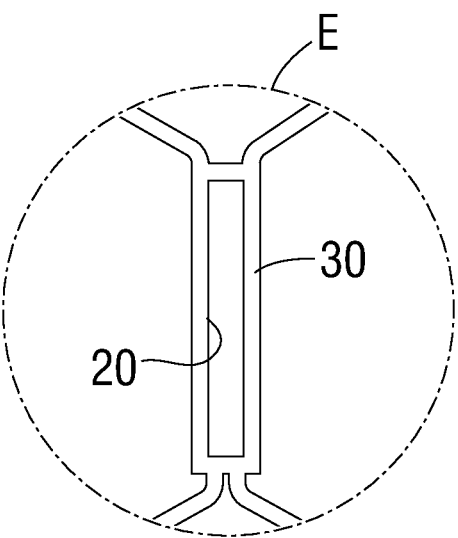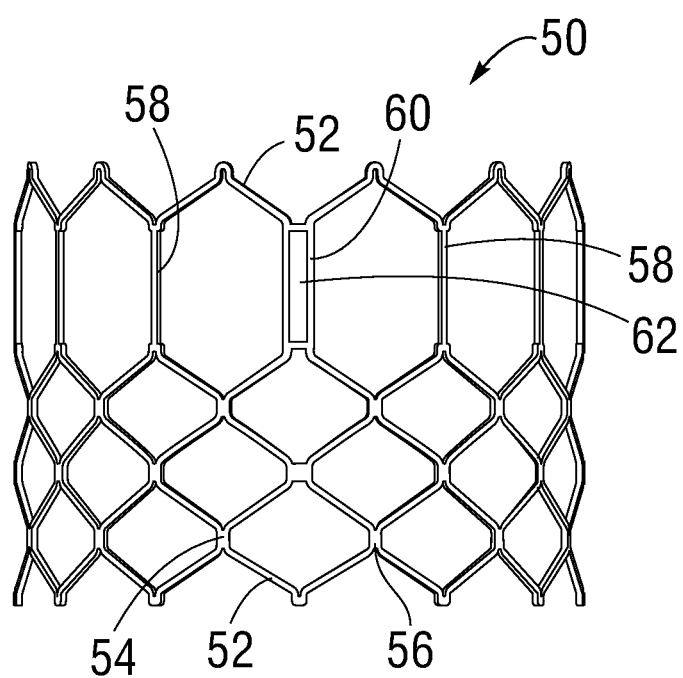

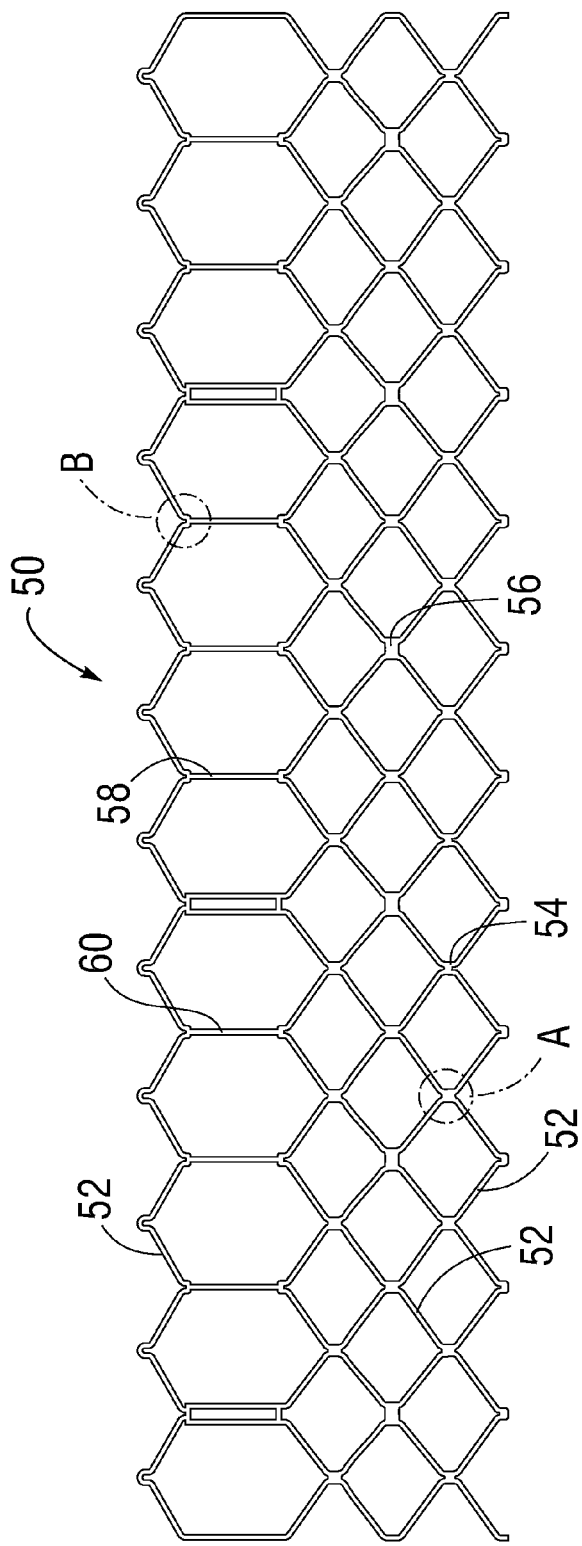
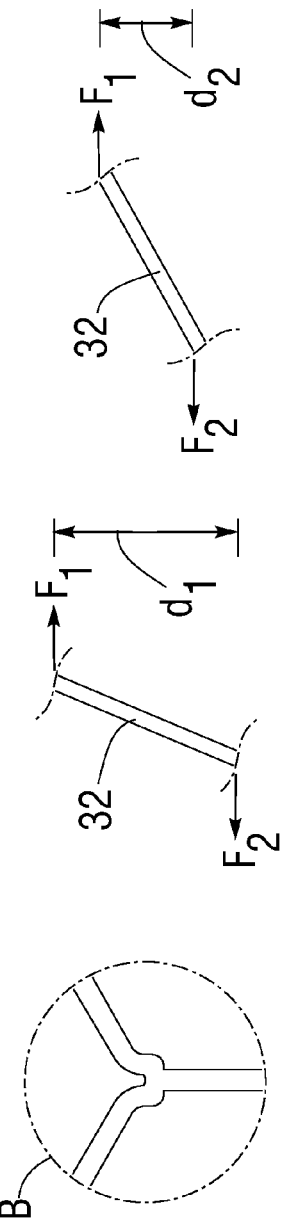
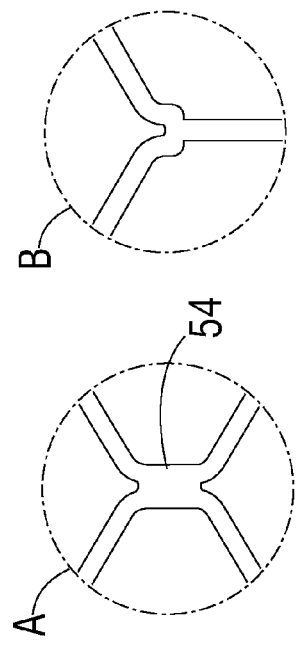

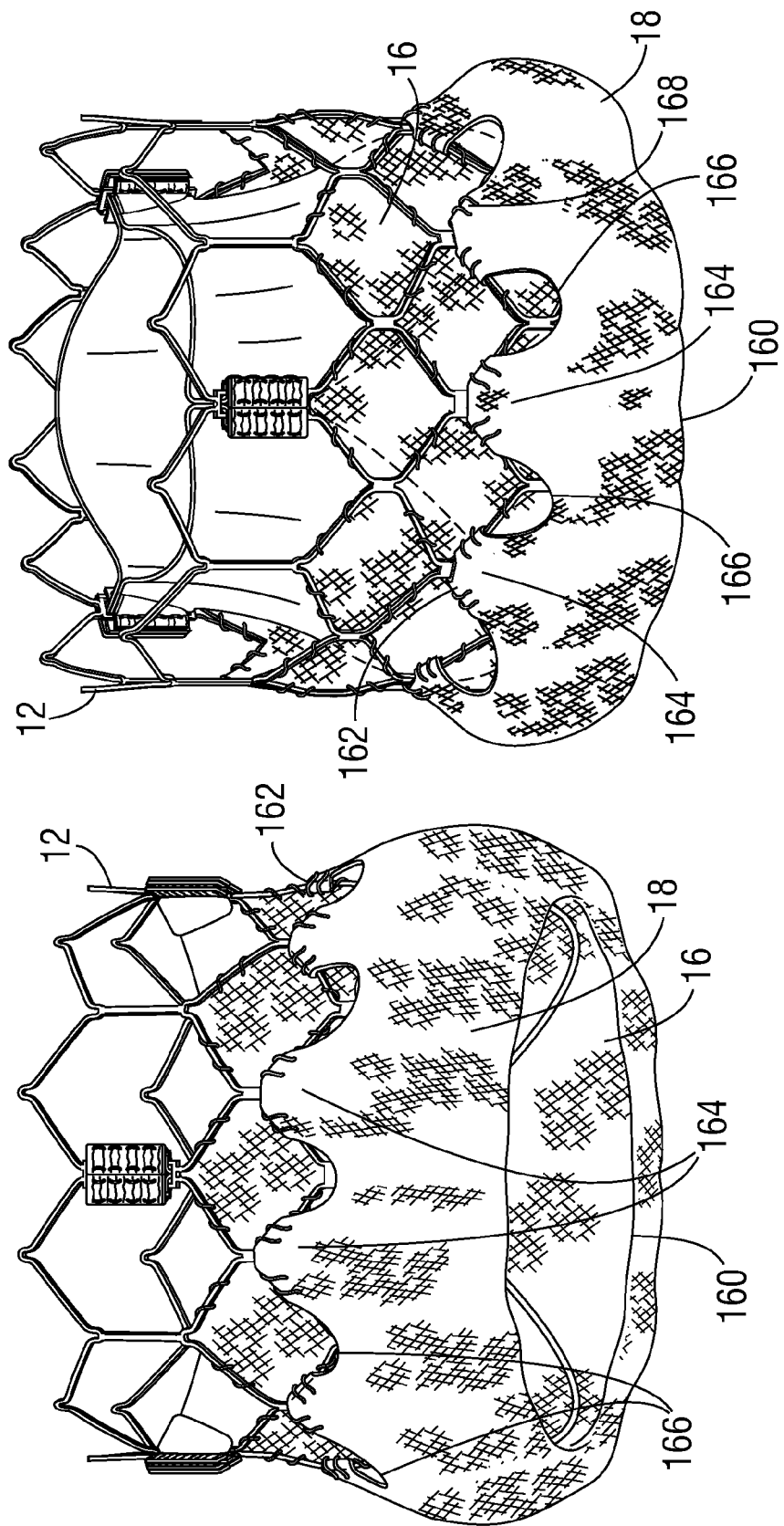

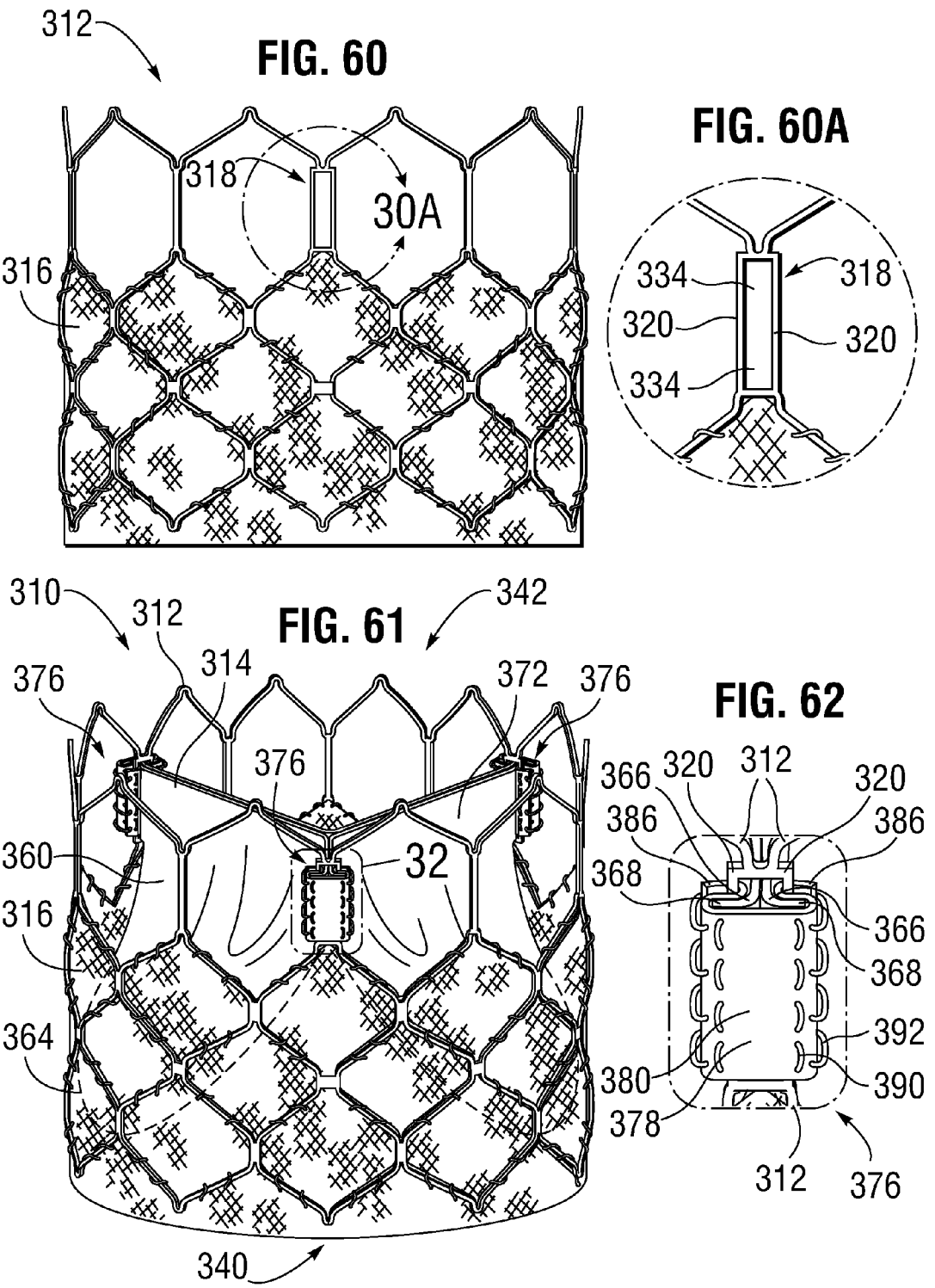

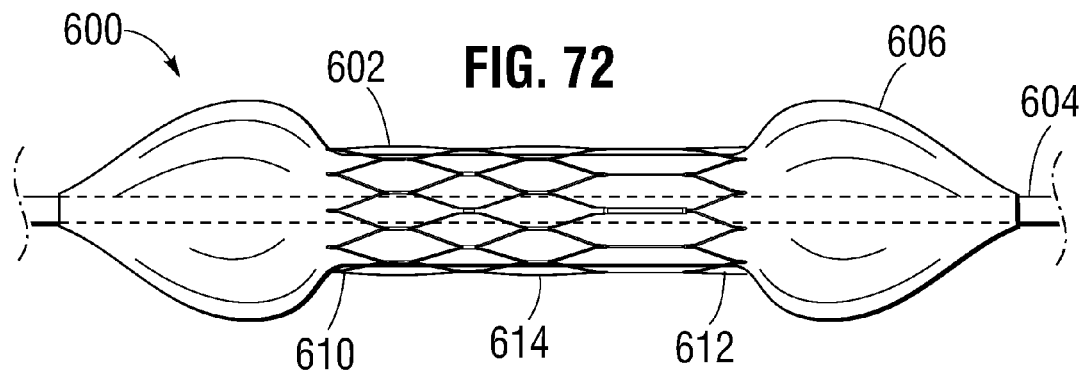
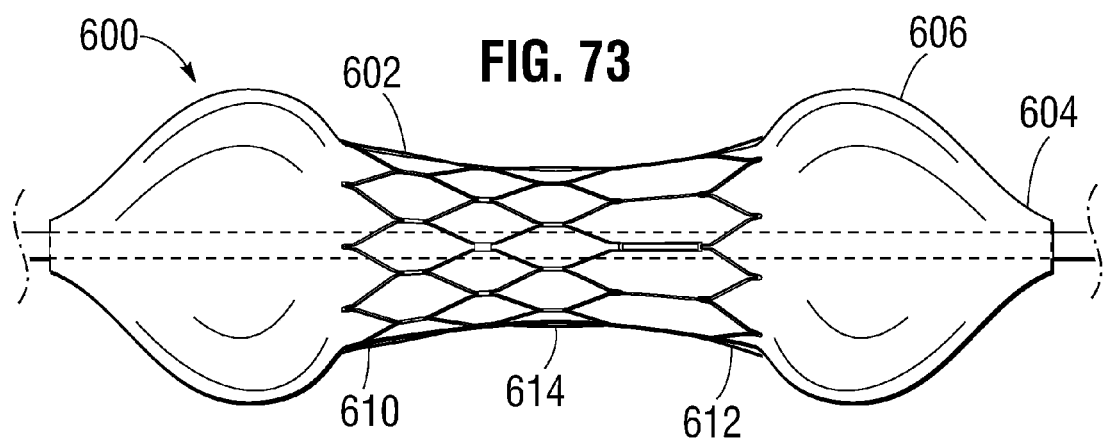
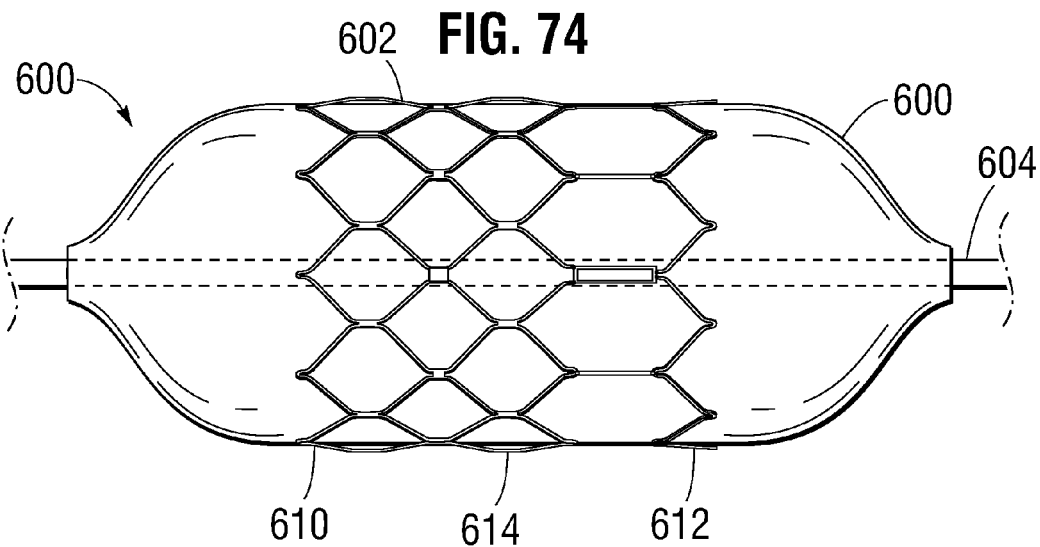

PROSTHETIC HEART VALVE

CROSS REFERENCE TO RELATED APPLICATIONS

This application claims the benefit of U.S. Provisional Application No. 61/390,107, entitled "COMMISSURE ATTACHMENT FOR PROSTHETIC VALVE," filed Oct. 5, 2010, and U.S. Provisional Application No. 61/508,513, entitled "PROSTHETIC HEART VALVE," filed Jul. 15, 2011, both of which applications are herein incorporated by reference.

FIELD

The present disclosure concerns embodiments of a prosthetic heart valve, and delivery systems for implanting heart valves.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is the diameter of the folded or crimped profile. The diameter of the crimped profile is important because it directly influences the physician's ability to advance the transcatheter heart valve through the femoral artery or vein. More particularly, a smaller profile allows for treatment of a wider population of patients, with enhanced safety.

SUMMARY

The present disclosure is directed toward methods and apparatuses relating to prosthetic valves, such as heart valves, delivery apparatuses, and assemblies of heart valves mounted on delivery apparatuses.

An exemplary embodiment of an assembly for implanting a prosthetic heart valve in a patient's body comprises a delivery apparatus comprising an elongated shaft and a radially expandable prosthetic heart valve mounted on the shaft in a radially collapsed configuration for delivery into the body. The prosthetic heart valve comprises an annular frame having an inflow end portion and an outflow end portion, and a leaflet structure positioned within the frame. The outer diameter of the inflow end portion of the frame is smaller than the outer diameter of the outflow end portion of the frame. The reduced diameter of the inflow end can be due to a reduce amount of materials positioned within the inflow end portion of the frame. The reduced diameter at the inflow end portion can make room for an outer skirt positioned around the inflow end portion.

In some embodiments, the heart valve can further comprise an outer skirt positioned around an outer surface of the inflow end portion of the frame such that an outer diameter of an inflow end portion of the prosthetic valve, inclusive of the outer skirt, is still less than or equal to an outer diameter of an outflow end portion of the prosthetic valve.

In some embodiments, the leaflet structure can comprise a plurality of leaflets that each comprises opposing side tabs on opposite sides of the leaflet. The side tabs can be secured to the outflow end portion of the frame. Each leaflet can further comprise a free outflow edge portion extending between the side tabs adjacent to the outflow end of the frame and an inflow edge portion extending between the side tabs adjacent to the inflow end of the frame. The inflow edge portion can comprise opposing axial edge portions that extend from the side tabs toward the inflow end in a generally axial direction and an intermediate edge portion that extends between the axial edge portions. The intermediate edge portion can comprise a curved apex portion adjacent to the inflow end of the frame and a pair of oblique portions that extend between the axial edge portions and the apex portion. The oblique portions can have a greater radius of curvature than the apex portion, forming a generally V-shaped leaflet.

In some embodiments, the frame comprises a plurality of angularly spaced commissure windows each comprising an enclosed opening between first and second axially oriented side struts. In these embodiments, the leaflet structure comprises a plurality of leaflets each comprising two opposing side tabs, each side tab being paired with an adjacent side tab of an adjacent leaflet to form commissures of the leaflet structure. Each commissure extends radially outwardly through a corresponding commissure window of the frame to a location outside of the frame and is sutured to the side struts of the commissure window. In some of these embodiments, the commissure windows of the frame are depressed radially inwardly relative to the portions of the frame extending between adjacent commissure windows when the prosthetic valve is in the collapsed configuration on the shaft.

In some embodiments, the frame comprises an inflow row of openings at the inflow end portion of the frame, an outflow row of openings at the outflow end portion of the frame, and at least one intermediate row of openings between the inflow row of openings and outflow row of openings. The openings of the inflow row of openings are larger than the openings of the at least one intermediate row of openings.

In some embodiments, portions of the leaflet structure protrude through openings in the frame while in the collapsed configuration on the shaft.

In some embodiments, the inflow end portion of the frame comprises a frame thickness that is less than a frame thickness of an intermediate portion of the frame between the inflow end portion and the outflow end portion.

Embodiments disclosed here can comprise an implantable prosthetic valve that is radially collapsible to a collapsed configuration and radially expandable to an expanded configuration. Such prosthetic valves can comprise an annular frame, a leaflet structure positioned within the frame, and an annular outer skirt positioned around an outer surface of the frame. The outer skirt can comprise an inflow edge secured to the frame at a first location, an outflow edge secured to the frame at a second location, and an intermediate portion between the inflow edge and the outflow edge. When the valve is in the expanded configuration, the intermediate portion of the outer skirt comprises slack in the axial direction between the inflow edge of the outer skirt and the outflow edge of the outer skirt, and when the valve is collapsed to the collapsed configuration, the axial distance between the inflow edge of the outer skirt and the outflow edge of the outer skirt increases, reducing the slack in the outer skirt in the axial direction.

In some of these embodiments, the outer skirt is not stretched in the axial direction when the valve is radially collapsed to the collapsed configuration and slack is removed from the intermediate portion of the outer skirt.

Some embodiments of an implantable prosthetic valve comprise an annular frame comprising a plurality of leaflet attachment portions, and a leaflet structure positioned within the frame and secured to the leaflet attachment portions of the frame. The leaflet structure comprises a plurality of leaflets, each leaflet comprising a body portion, two opposing primary side tabs extending from opposite sides of the body portion, and two opposing secondary tabs extending from the body adjacent to the primary side tabs. The secondary tabs are folded about a radially extending crease such that a first portion of the secondary tabs lies flat against the body portion of the respective leaflet, and the secondary tabs are folded about an axially extending crease such that a second portion of the secondary tabs extends in a different plane than the first portion. The second portion of each secondary tab is sutured to a respective primary tab and the secondary tabs are positioned inside of the frame.

In some of these embodiments, the first portion of each the secondary tab pivots about the axially extending crease and lays flat against the second portion of the secondary tab when the valve is collapsed to a radially collapsed configuration. The first portion of each secondary tab comprises an inner edge spaced radially from an inner surface of the frame, and the body portion of the leaflet articulates about the inner edges of the two secondary tabs of the leaflet in response to blood flowing through the valve when the valve is in operation within a patient's body.

Some embodiments disclosed herein comprise an implantable prosthetic valve that is radially collapsible to a collapsed configuration and radially expandable to an expanded configuration. The prosthetic valve comprises an annular frame having an inflow end portion and an outflow end portion, a leaflet structure positioned within the frame, and an annular inner skirt positioned within the frame. The inner skirt is secured to the inside of the frame and the inner skirt comprises a weave of a first set of strands with a second set of strands, both the first and second sets of strands being non-parallel with the axial direction of the valve. When the valve is collapsed from the expanded configuration to the collapsed configuration, the axial length of the frame increases and the both the first and second sets of strands rotate toward the axial direction of the valve, allowing the inner skirt to elongate in the axial direction along with the frame.

In some of these embodiments, the first set of strands are substantially perpendicular to the second set of strands when the valve is in the expanded configuration. In some embodiments, the first set of strands forms a first angle with the axial direction of the valve and the second set of strands forms a second angle with the axial direction of the valve, the first and second angles being substantially equal. In some of these embodiments, the first and second sets of strands comprise 20-denier yarn.

Some embodiments of an implantable prosthetic valve comprise a radially collapsible and expandable annular frame comprising a plurality of angularly spaced commissure windows each comprising an enclosed opening between first and second axially oriented side struts. The valve also comprises a leaflet structure positioned within the frame and comprising a plurality of leaflets each comprising two opposing side tabs. Each side tab is paired with an adjacent side tab of an adjacent leaflet to form commissures of the leaflet structure. Each pair of side tabs extends radially outwardly through a corresponding commissure window to a location outside of the frame, the portions of the tabs located outside of the frame extending circumferentially away from one another and along an exterior surface of the side struts. The valve further comprises a plurality of wedges, each wedge being positioned between the side struts of a commissure window and separating the pair of side tabs extending through the commissure window, the wedge being urged radially inwardly against the side tabs.

The wedges can be elongated in an axial direction and correspond in axial length with an axial length of the side struts of the commissure windows. The wedges can further restrict rotational movement of the pair of side tabs relative to the commissure window. Each wedge can be sutured to a flexible reinforcing sheet that is also sutured to each of the pair of side tabs, and each can be sutured to the pair of side tabs. The wedges can comprise a non-metallic material, such as suture material.

The foregoing and other objects, features, and advantages of the invention will become more apparent from the following detailed description, which proceeds with reference to the accompanying figures.

BRIEF DESCRIPTION OF THE DRAWINGS

FIGS. 4-10 show an exemplary frame of the heart valve of FIG. 1.

FIGS. 11-15B show another exemplary frame for use in a prosthetic heart valve.

FIGS. 42 and 43 show the exemplary prosthetic heart valve of FIG. 1.

FIG. 60 is a side view of an embodiment of a frame of a valve having commissure windows, prior to mounting a leaflet structure to the frame.

FIG. 60A is an enlarged side view of one commissure window of FIG. 60.

FIG. 61 is a perspective view of an embodiment of a prosthetic valve comprising the frame of FIG. 60 and a leaflet structure mounted to the valve.

FIG. 62 is an enlarged side view of one commissure of the valve of FIG. 61.

FIGS. 72-74 show balloon expansion of an alternative embodiment of a frame for a prosthetic valve having inflow and outflow end portions of reduced thickness.

DETAILED DESCRIPTION

Figure 1:
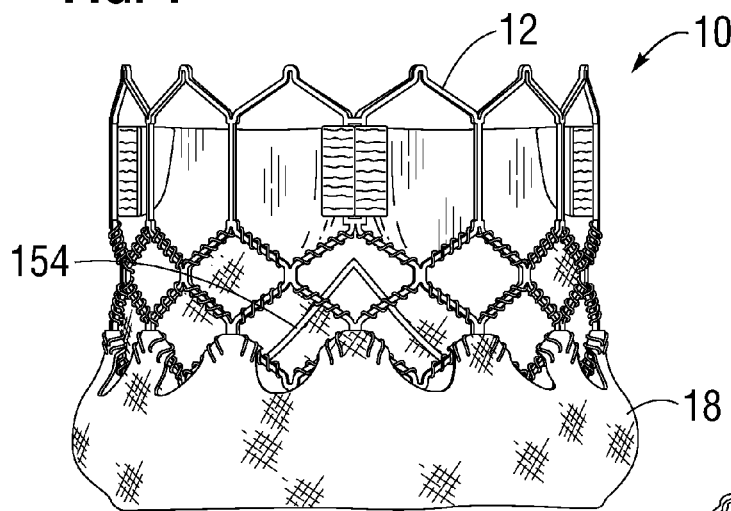
FIGS. 1-3 show an exemplary embodiment of a prosthetic heart valve.
Figure 2:
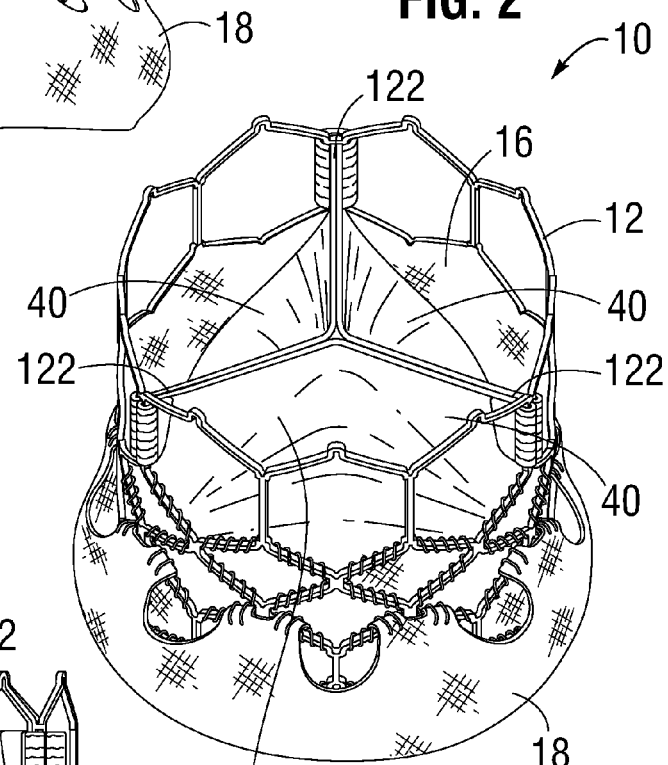
Figure 3:
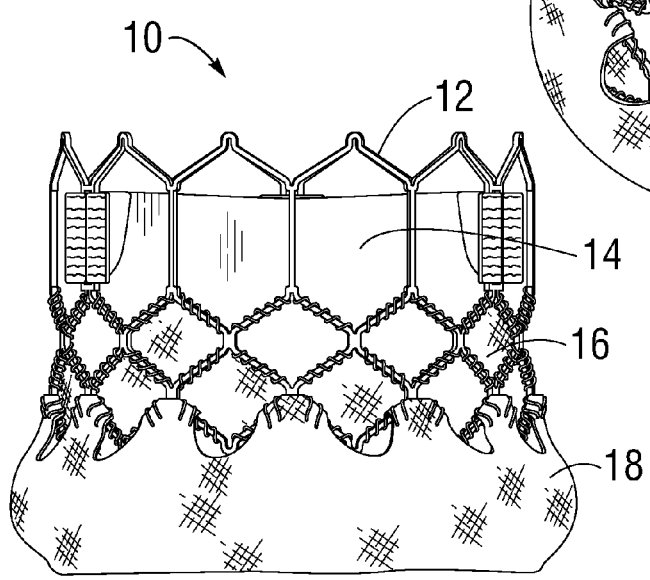

FIGS. 1-3 show various views of a prosthetic heart valve 10, according to one embodiment. The illustrated valve is adapted to be implanted in the native aortic annulus, although in other embodiments it can be adapted to be implanted in the other native annuluses of the heart. The valve 10 can have four main components: a stent, or frame, 12, a valvular structure 14, an inner skirt 16, and an outer skirt 18.

The valvular structure 14 can comprise three leaflets 40, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 1 tracks the scalloped shape of the leaflet structure). By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 12 is shown in FIG. 4. The frame 12 can be formed with a plurality of circumferentially spaced slots, or commissure windows, 20 (three in the illustrated embodiment) that are adapted to mount the commissures of the valvular structure 14 to the frame, as described in greater detail below. The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the valve 10) can be crimped to a radially compressed state on a delivery catheter and then expanded inside a patient by an inflatable balloon or equivalent expansion mechanism. When constructed of a self-expandable material, the frame 12 (and thus the valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9 and 10 are enlarged views of the portions of the frame 12 identified by letters A, B, C, D and E, respectively, in FIG. 4.

Each commissure window frame portion 30 mounts a respective commissure of the leaflet structure 14. As can be seen each frame portion 30 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

Figure 18:
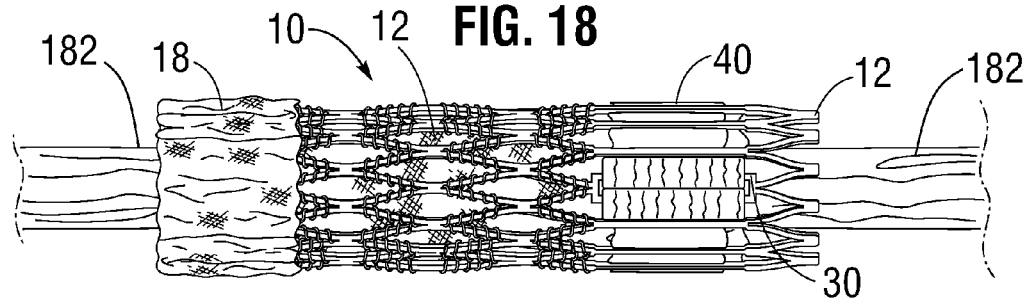
FIG. 18 shows the heart valve of FIG. 1 in a compressed state and mounted on an exemplary balloon catheter.
Figure 53:
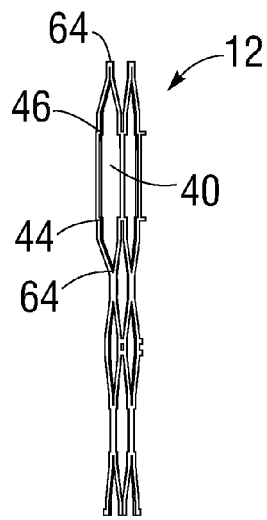
FIG. 53 shows a portion of the frame of FIG. 4 in a radially compressed state.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. FIG. 53 shows a portion of the frame 12 in a crimped state. The junctions 44, 46, along with junctions 64, prevent full closure of openings 40. FIG. 18 shows the valve 10 crimped on a balloon catheter. As can be seen, the geometry of the struts 31, and junctions 44, 46 and 64 assists in creating enough space in openings 40 in the crimped state to allow portions of the leaflets to protrude (i.e., bulge) outwardly through openings. This allows the valve to be crimped to a relatively smaller diameter than if all of the leaflet material is constrained within the crimped frame.

The frame 12 is configured to prevent or at least minimize possible over-expansion of the valve at a predetermined balloon pressure, especially at the outflow end portion of the frame, which supports the leaflet structure 14. In one aspect, the frame is configured to have relatively larger angles 42a, 42b, 42c, 42d, 42e between struts. The larger the angle, the greater the force required to open (expand) the frame. This phenomenon is schematically illustrated in FIGS. 15A and 15B. FIG. 15A shows a strut 32 when the frame 12 is in its compressed state (e.g., mounted on a balloon). The vertical distance $d_1$ between the ends of the struts is greatest when the frame is compressed, providing a relatively large moment between forces $F_1$ and $F_2$ acting on the ends of the strut in opposite directions upon application of an opening force from inflation of the balloon (or expansion of another expansion device). When the frame expands radially, the vertical distance between the ends of the strut decreases to a distance $d_2$, as depicted in FIG. 15B. As the vertical distance decreases, so does the moment between forces $F_1$ and $F_2$. Hence, it can be seen that a relatively greater expansion force is required as the vertical distance and the moment between the ends of the strut decreases. Moreover, strain hardening (stiffening) at the ends of the strut increases as the frame expands, which increases the expansion force required to induce further plastic deformation at the ends of the strut. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are at least 120 degrees or greater when the frame is expanded to its functional size.

Figure 55:
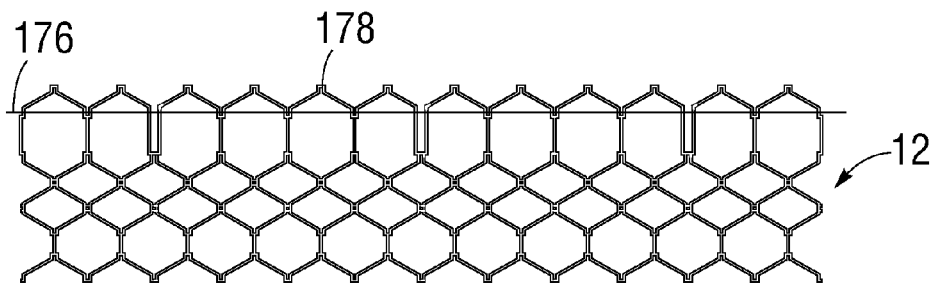
FIG. 55 shows the frame of FIG. 4 in an unrolled, flat configuration.

In addition, the inflow and outflow ends of a frame generally tend to over-expand more so than the middle portion of the frame due to the "dog boning" effect of the balloon used to expand the valve. To protect against over-expansion of the leaflet structure 14, the leaflet structure desirably is secured to the frame 12 below the upper row of struts 32, as best shown in FIG. 1. FIG. 55 shows a flattened view of the frame 12 similar to FIG. 5, but showing a line 176 superimposed over the frame to indicate the position of the upper edges of the leaflets 40. Thus, in the event that the outflow end of the frame is over-expanded, the leaflet structure is positioned at a level below where over-expansion is likely to occur, thereby protecting the leaflet structure from over-expansion.

Figure 56:
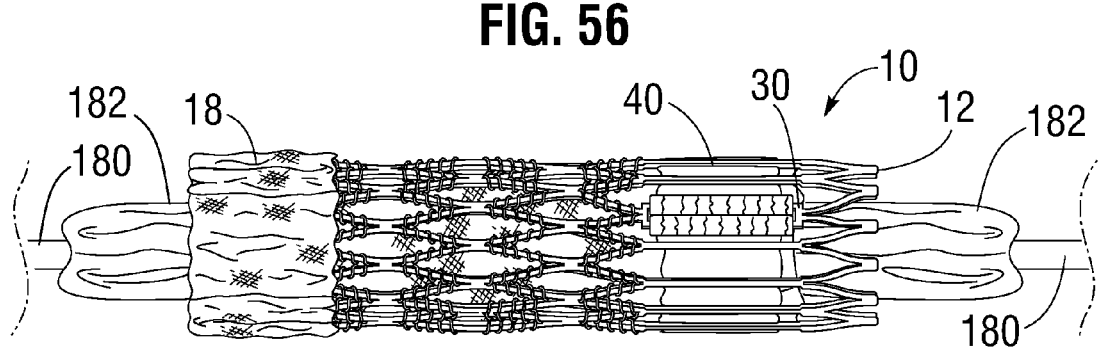
FIG. 56 shows the heart valve of FIG. 1 in a compressed state and mounted on an exemplary balloon catheter.

In a known valve construction, the leaflets can protrude outwardly beyond the outflow end of the frame when the valve is crimped if the leaflets are mounted too close to the distal end of the frame. If the delivery catheter on which the crimped valve is mounted includes a pushing mechanism or stop member that pushes against or abuts the outflow end of the valve (for example, to maintain the position of the crimped valve on the delivery catheter), the pushing member or stop member can damage the exposed leaflets that extend beyond the outflow end of the frame. Another benefit of mounting the leaflets at a location spaced from the outflow end 178 of the frame is that when the valve is crimped on a delivery catheter, as shown in FIG. 56, the leaflets 40 do not protrude beyond the outflow end 178 of the frame in the axial direction. As such, if the delivery catheter includes a pushing mechanism or stop member that pushes against or abuts the outflow end of the valve, the pushing mechanism or stop member can contact the end 178 of the frame, and not leaflets 40, so as to avoid damage to the leaflets.

Figure 54:
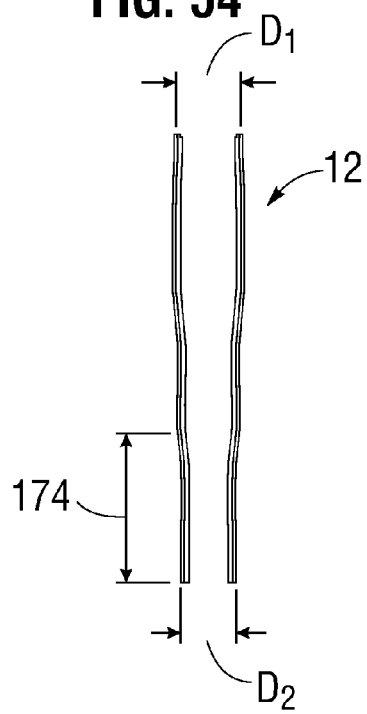
FIG. 54 shows a cross-sectional profile of the frame of FIG. 4, showings a general tapering from the outflow end to the inflow end.

Also, as can be seen in FIG. 5, the openings 36 of the lowermost row of openings in the frame are relatively larger than the openings 38 of the two intermediate rows of openings. As shown in FIG. 54, this allows the frame, when crimped, to assume an overall tapered shape that tapers from a maximum diameter $D_1$ at the outflow end of the valve to a minimum diameter $D_2$ at the inflow end of the valve. When crimped, the frame 12 has a reduced diameter region extending along a portion of the frame adjacent the inflow end of the frame, indicated by reference number 174, that generally corresponds to the region of the frame covered by the outer skirt 18. The diameter of region 174 is reduced compared to the diameter of the upper portion of the frame (which is not covered by the outer skirt) such that the outer skirt 18 does not increase the overall crimp profile of the valve. When the valve is deployed, the frame can expand to the cylindrical shape shown in FIG. 4. In one example, the frame of a 26-mm valve, when crimped, had a diameter $D_1$ of 14 French at the outflow end of the valve and a diameter $D_2$ of 12 French at the inflow end of the valve.

FIGS. 11 and 12 show an alternative frame 50 that can be incorporated in the valve 10. The frame 50 comprises multiple rows of circumferentially extending, angled struts 52 that are connected to each other at nodes, or connecting portions, 54 and 56. The uppermost row of struts 52 are connected to an adjacent row of struts by a plurality of axially extending struts 58 and commissure window frame portions 60. Each commissure frame portion 60 defines a slot, or commissure window, 62 for mounting a respective commissure of the valvular structure, as described in greater detail below. In particular embodiments, the thickness T of the frame 50 is about 0.45 mm or less. FIGS. 13 and 14 are enlarged views of the portions of the frame 50 identified by letters A and B, respectively, in FIG. 12.

The main functions of the inner skirt 16 are to assist in securing the valvular structure 14 to the frame 12 and to assist in forming a good seal between the valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic or natural materials can be used. The thickness of the skirt desirably is less than 6 mil, and desirably less than 4 mil, and even more desirably about 2 mil. In particular embodiments, the skirt 16 can have a variable thickness, for example, the skirt can be thicker at its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

Figure 38:
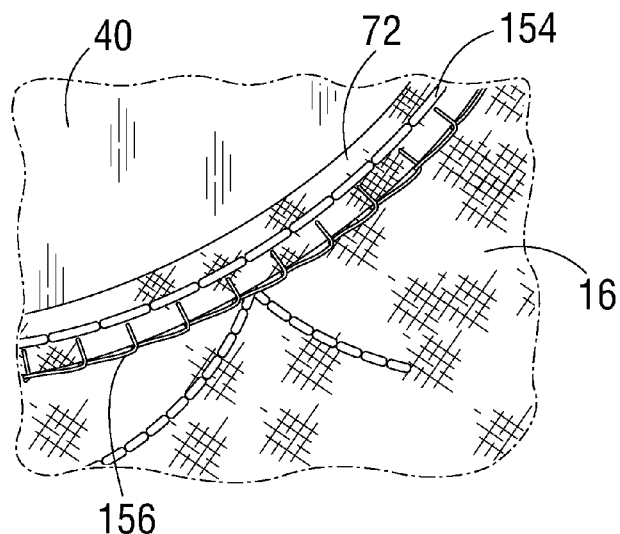
Figure 39:
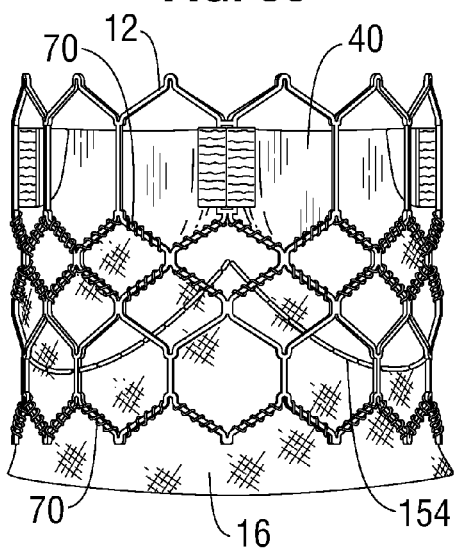

The skirt 16 can be secured to the inside of frame 12 via sutures 70, as shown in FIG. 39. Valvular structure 14 can be attached to the skirt via one or more thin PET reinforcing strips 72 (which collectively can form a sleeve), discussed below, which enables a secure suturing and protects the pericardial tissue of the leaflet structure from tears. Valvular structure 14 can be sandwiched between skirt 16 and the thin PET strips 72 as shown in FIG. 38. Sutures 154, which secure the PET strip and the leaflet structure 14 to skirt 16, can be any suitable suture, such as an Ethibond suture. Sutures 154 desirably track the curvature of the bottom edge of leaflet structure 14, as described in more detail below.

Known fabric skirts comprise a weave of warp and weft fibers that extend perpendicular to each other and with one set of fibers extending perpendicularly to the upper and lower edges of the skirt. When the metal frame, to which the fabric skirt is secured, is radially compressed, the overall axial length of the frame increases. Unfortunately, a fabric skirt, which inherently has limited elasticity, cannot elongate along with the frame and therefore tends to deform the struts of the frame and prevents uniform crimping.

Figure 17:
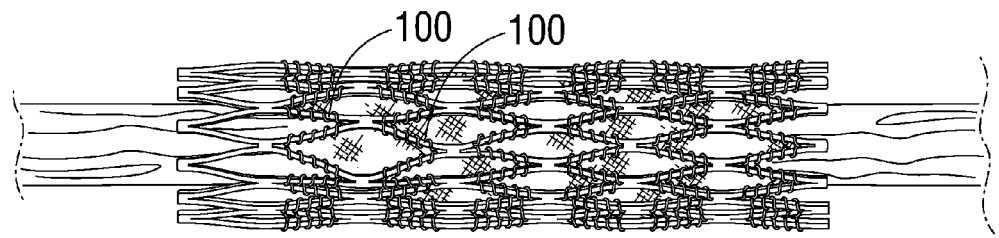
FIG. 17 shows another embodiment of a prosthetic heart valve in a compressed (crimped) condition with a deformed frame.

FIG. 17 shows an example of a crimped valve where the struts have been deformed in several places, as indicated by reference number 100, by a skirt having fibers that extend perpendicular to the upper and lower edges of the skirt. Moreover, the fabric tends to bunch or create bulges of excess material in certain locations, which limits the minimum crimping profile and prevents uniform crimping.

Figure 16A:
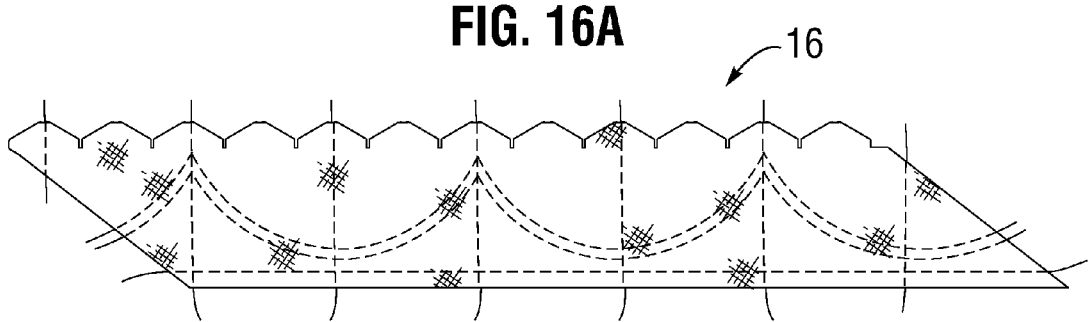
FIGS. 16A and 16B show an exemplary inner skirt of the heart valve of FIG. 1.
Figure 16B:
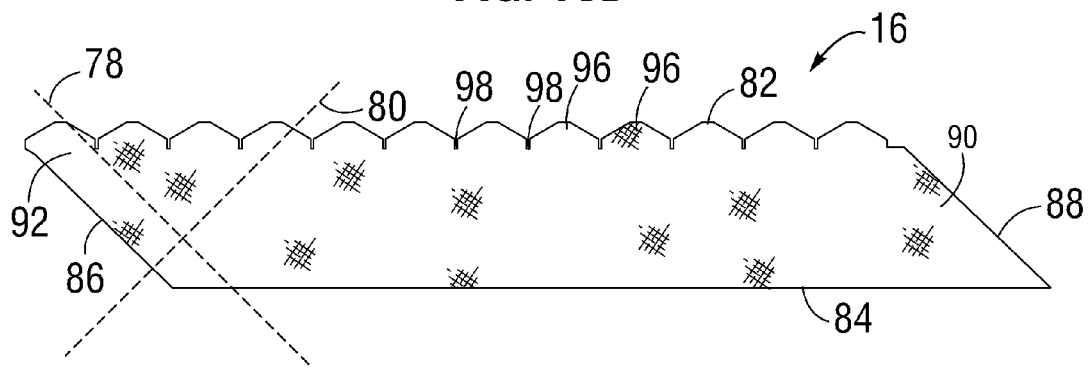

Referring to FIG. 16B, in contrast to known fabric skirts, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees relative to the upper and lower edges 82, 84. The skirt 16 can be formed by weaving the fibers at 45 degree angles relative to the upper and lower edges of the fabric. Alternatively, the skirt can be diagonally cut from a vertically woven fabric (where the fibers extend perpendicular to the edges of the material) such that the fibers extend at 45 degree angles relative to the cut upper and lower edges of the skirt. As further shown in FIG. 16B, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall shape of the skirt is that of a rhomboid.

Figure 19A:
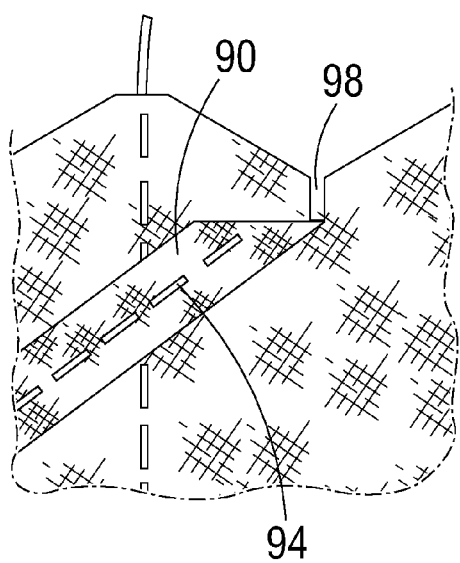
FIGS. 19-20 show the assembly of the inner skirt of FIG. 16A with the frame of FIG. 4.
Figure 19B:
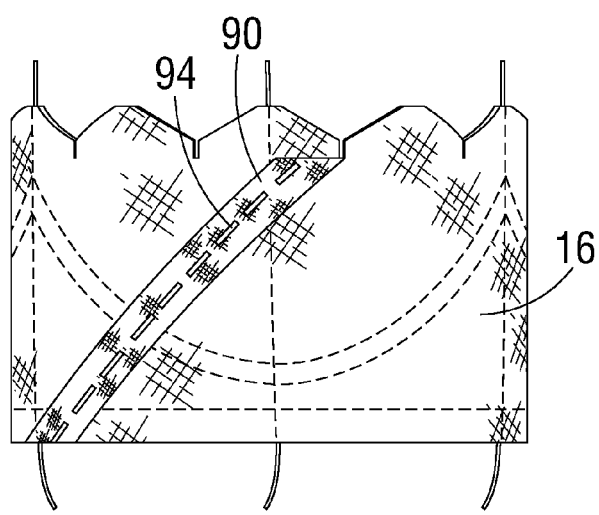
Figure 20:
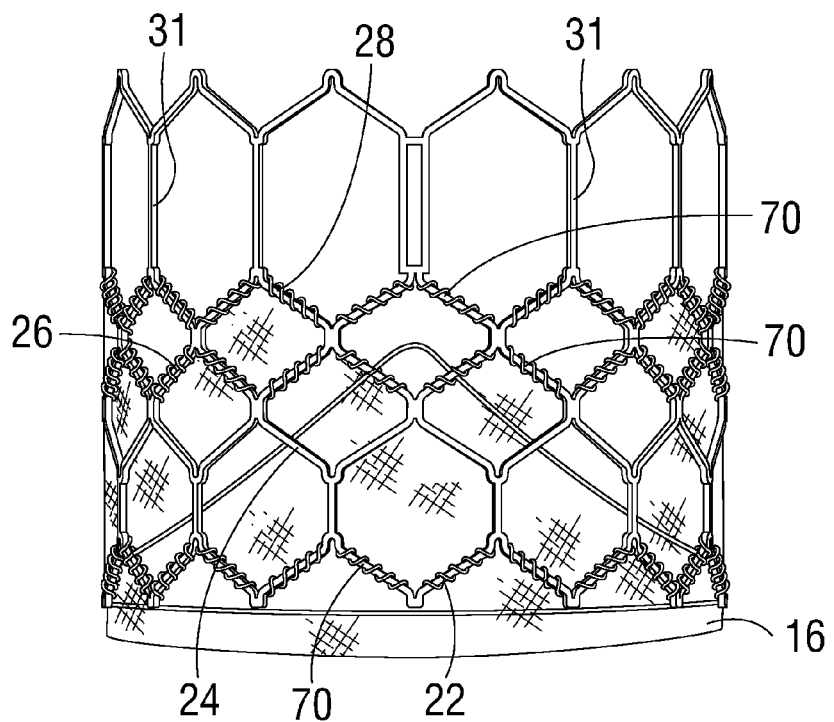

FIGS. 19A and 19B shows the skirt 16 after opposing edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to edges 86, 88. The upper edge portion of the skirt 16 can be formed with a plurality of projections 96 that define an undulated shape that generally follows the shape of the fourth row of struts 28 immediately adjacent the lower ends of axial struts 31. In this manner, as best shown in FIG. 20, the upper edge of skirt 16 can be tightly secured to struts 28 with sutures 70. Skirt 16 can also be formed with slits 98 to facilitate attachment of the skirt to the frame. Slits 98 are dimensioned so as to allow an upper edge portion of skirt to be partially wrapped around struts 28 and reduce stresses in the skirt during the attachment procedure. For example, in the illustrated embodiment, skirt 16 is placed on the inside of frame 12 and an upper edge portion of the skirt is wrapped around the upper surfaces of struts 28 and secured in place with sutures 70. Wrapping the upper edge portion of the skirt around struts 28 in this manner provides for a stronger and more durable attachment of the skirt to the frame. The skirt 16 can also be secured to the first, second, and third rows of struts 22, 24, and 26, respectively, with sutures 70.

Referring again to FIG. 16B, due to the orientation of the fibers relative to the upper and lower edges, the skirt can undergo greater elongation in the axial direction (i.e., in a direction from the upper edge 82 to the lower edge 84).

Thus, when the metal frame 12 is crimped (as shown in FIG. 18), the skirt 16 can elongate in the axial direction along with the frame and therefore provides a more uniform and predictable crimping profile. Each cell of the metal frame in the illustrated embodiment includes at least four angled struts that rotate towards the axial direction (i.e., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the valve is crimped.

In addition, the spacing between the woven fibers or yarns can be increased to facilitate elongation of the skirt in the axial direction. For example, for a PET skirt 16 formed from 20-denier yarn, the yarn density can be about 15% to about 30% less than a conventional PET skirt. In some examples, the yarn spacing of the skirt 16 can be from about 155 yarns per inch to about 180 yarns per inch, such about 160 yarns per inch, whereas in a conventional PET skirt the yarn spacing can be from about 217 yarns per inch to about 247 yarns per inch. The oblique edges 86, 88 promote uniform and even distribution of the fabric material along inner circumference of the frame during crimping so as to minimize bunching of the fabric to facilitate uniform crimping to the smallest possible diameter. Additionally, cutting diagonal sutures in a vertical manner may leave loose fringes along the cut edges. The oblique edges 86, 88 help minimize this from occurring. As noted above, FIG. 17 shows a crimped valve with a conventional skirt that has fibers that run perpendicular to the upper and lower edges of the skirt. Comparing FIGS. 17 and 18, it is apparent that the construction of skirt 16 avoids undesirable deformation of the frame struts and provides more uniform crimping of the frame.

In alternative embodiments, the skirt can be formed from woven elastic fibers that can stretch in the axial direction during crimping of the valve. The warp and weft fibers can run perpendicular and parallel to the upper and lower edges of the skirt, or alternatively, they can extend at angles between 0 and 90 degrees relative to the upper and lower edges of the skirt, as described above.

Figure 28:
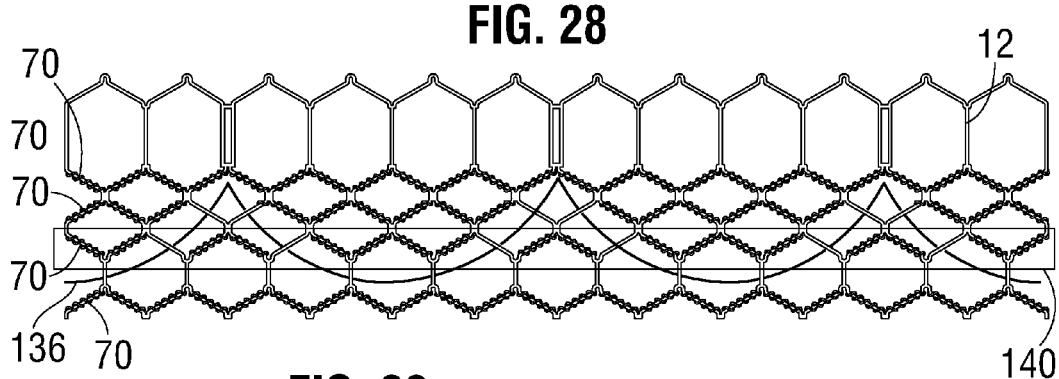

The inner skirt 16 can be sutured to the frame 12 at locations away from the suture line 154 so that the skirt can be more pliable in that area (see FIG. 28). This can avoid stress concentrations at the suture line 154, which attaches the lower edges of the leaflets to the skirt 16.

Figure 21:
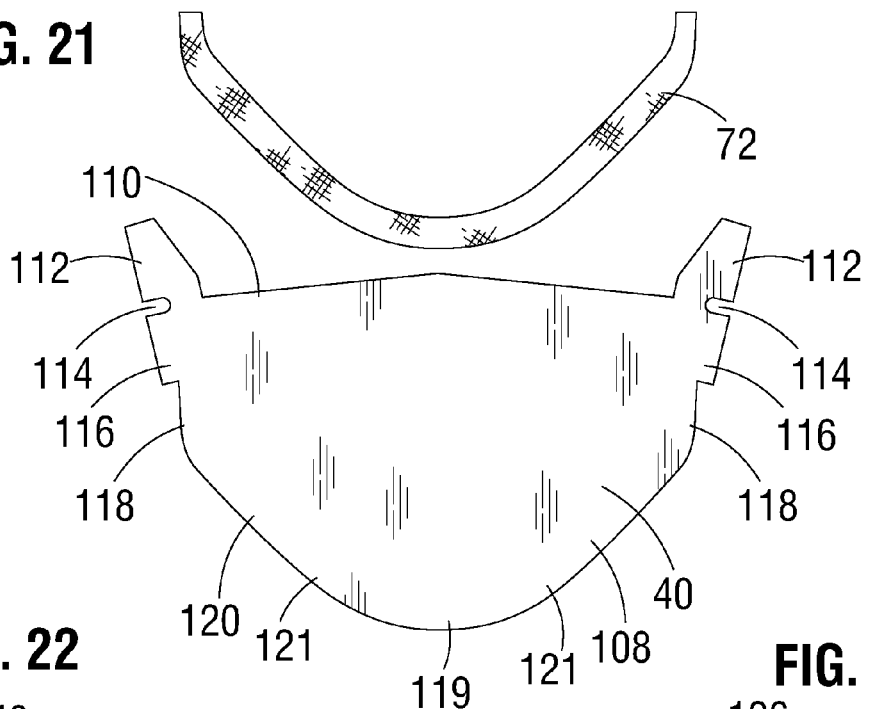
FIGS. 21-28 show the assembly of an exemplary leaflet structure.
Figure 22:
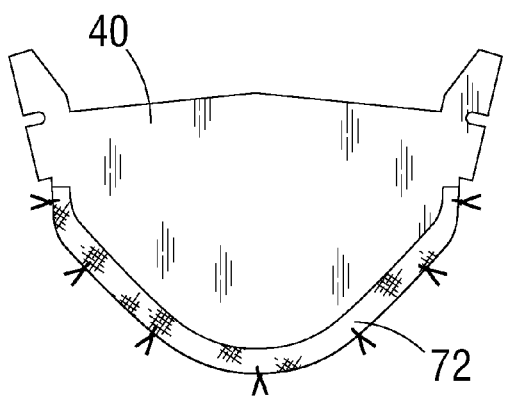

As noted above, the leaflet structure 14 in the illustrated embodiment includes three flexible leaflets 40 (although a greater or fewer number of leaflets can be used). As best shown in FIG. 21, each leaflet 40 in the illustrated configuration has an upper (outflow) free edge 110 extending between opposing upper tabs 112 on opposite sides of the leaflet. Below each upper tab 112 there is a notch 114 separating the upper tab from a corresponding lower tab 116. The lower (inflow) edge portion 108 of the leaflet extending between respective ends of the lower tabs 116 includes vertical, or axial, edge portions 118 on opposites of the leaflets extending downwardly from corresponding lower tabs 116 and a substantially V-shaped, intermediate edge portion 120 having a smooth, curved apex portion 119 at the lower end of the leaflet and a pair of oblique portions 121 that extend between the axial edge portions and the apex portion. The oblique portions can have a greater radius of curvature than the apex portion. Each leaflet 40 can have a reinforcing strip 72 secured (e.g., sewn) to the inner surface of the lower edge portion 108, as shown in FIG. 22.

Figure 23:
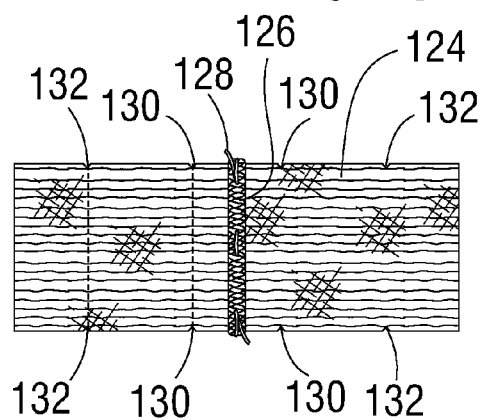

The leaflets 40 can be secured to one another at their adjacent sides to form commissures 122 of the leaflet structure. A plurality of flexible connectors 124 (one of which is shown in FIG. 23) can be used to interconnect pairs of adjacent sides of the leaflets and to mount the leaflets to the commissure window frame portions 30. The flexible connectors 124 can be made from a piece of woven PET fabric, although other synthetic and/or natural materials can be used. Each flexible connector 124 can include a wedge 126 extending from the lower edge to the upper edge at the center of the connector. The wedge 126 can comprise a non-metallic material, such as a rope or a piece of Ethibond 2-0 suture material, secured to the connector with a temporary suture 128. The wedge 126 helps prevent rotational movement of the leaflet tabs once they are secured to the commissure window frame portions 30. The connector 124 can have a series of inner notches 130 and outer notches 132 formed along its upper and lower edges.

Figure 24:
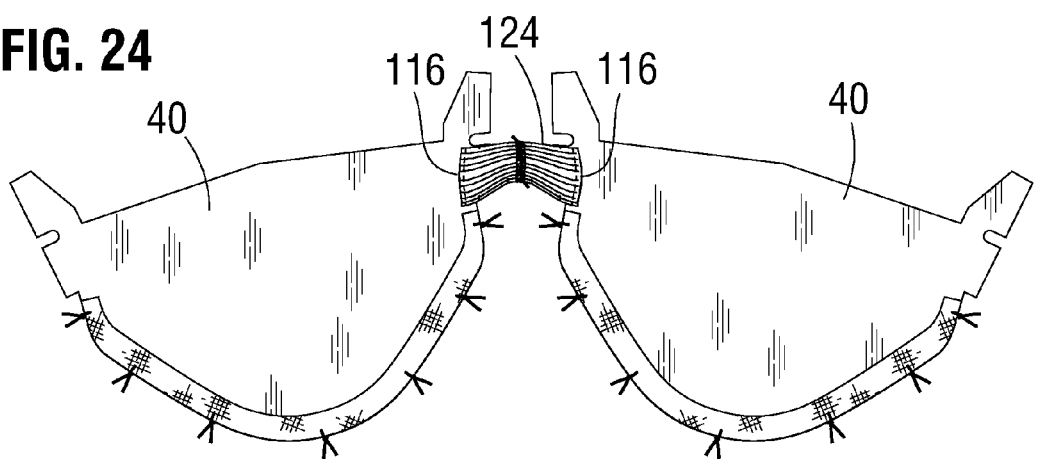
Figure 25:
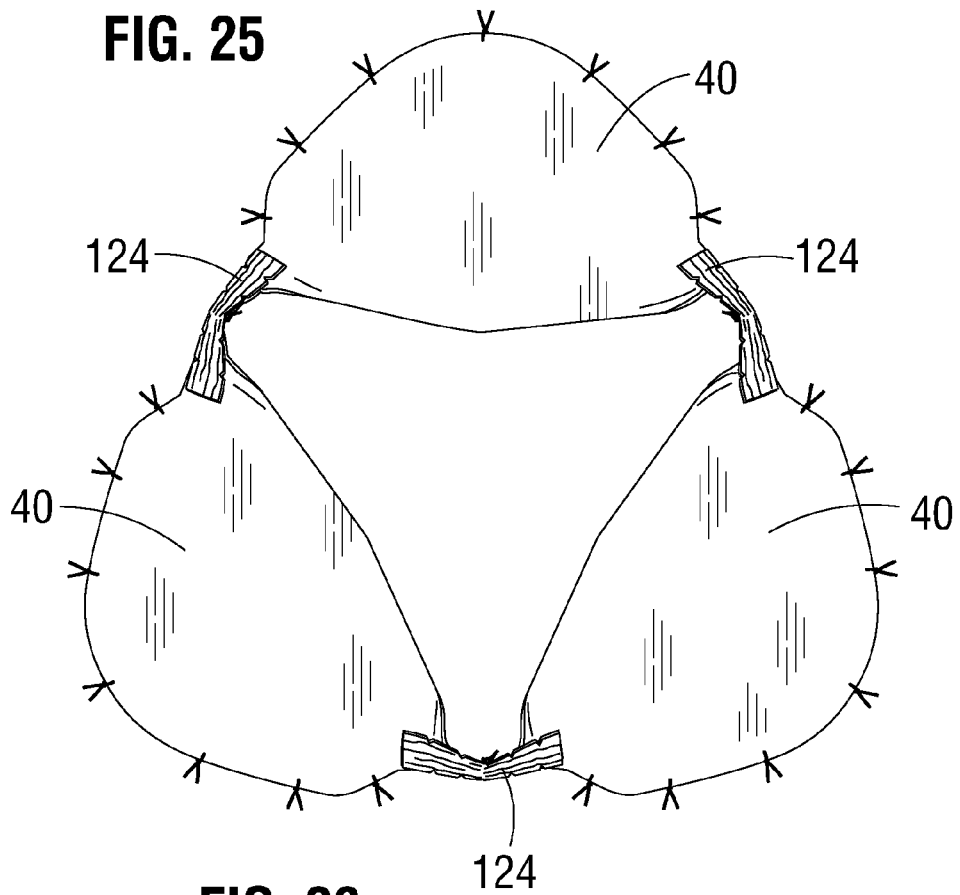

FIG. 24 shows the adjacent sides of two leaflets 40 interconnected by a flexible connector 124. The opposite end portions of the flexible connector 124 can be placed in an overlapping relationship with the lower tabs 116 with the inner notches 130 aligned with the vertical edges of the tabs 116. Each tab 116 can be secured to a corresponding end portion of the flexible connector 124 by suturing along a line extending from an outer notch 132 on the lower edge to an outer notch 132 on the upper edge of the connector. Three leaflets 40 can be secured to each other side-to-side using three flexible connectors 124, as shown in FIG. 25.

Figure 26:
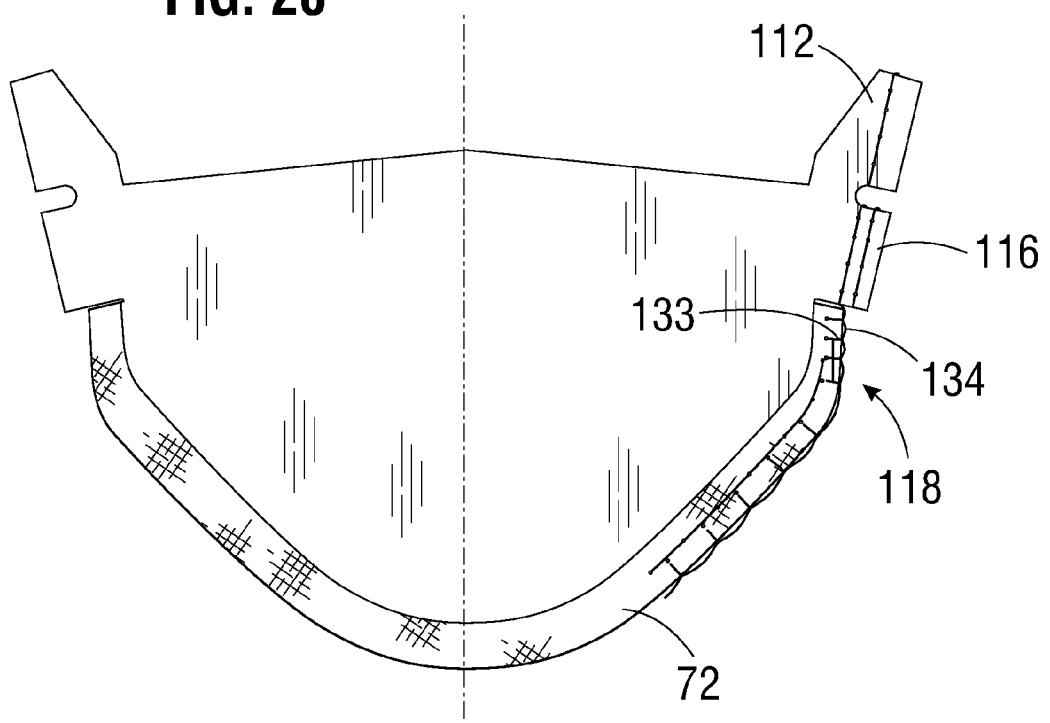
Figure 27:
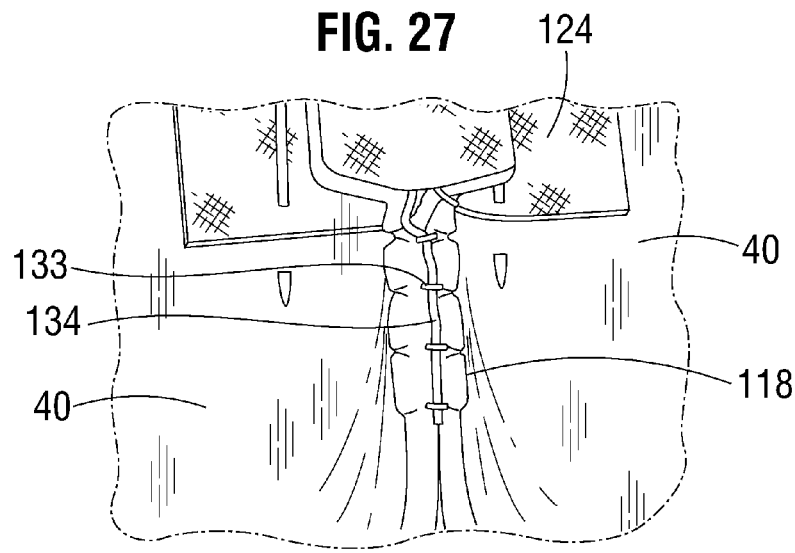

Referring now to FIGS. 26 and 27, the adjacent sub-commissure portions 118 of two leaflets can be sutured directly to each other. In the example shown, PTFE-6-0 suture material is used to form in-and-out stitches 133 and comb stitches 134 that extend through the sub-commissure portions 118 and the reinforcing strips 72 on both leaflets. The two remaining pairs of adjacent sub-commissure portions 118 can be sutured together in the same manner to form the assembled leaflet structure 14, which can then be secured to the frame 12 in the following manner.

As noted above, the inner skirt 16 can be used to assist in suturing the leaflet structure 14 to the frame. As shown in FIG. 28, the skirt 16 can have an undulating temporary marking suture 136 to guide the attachment of the lower edges of each leaflet 40. The skirt 16 itself can be sutured to the struts of the frame 12 using sutures 70, as noted above, before securing the leaflet structure 14 to the skirt 16. The struts that intersect the marking suture 136 desirably are not attached to the skirt 16. This allows the skirt 16 to be more pliable in the areas not secured to the frame and minimizes stress concentrations along the suture line that secures the lower edges of the leaflets to the skirt. The portion of the skirt 16 demarcated by rectangle 140 initially is left unsecured to the frame 12, and is later secured to the frame after the leaflet structure 14 is secured to the skirt, as further described below. As noted above, when the skirt is secured to the frame, the fibers 78, 80 of the skirt (see FIG. 16B) generally align with the angled struts of the frame to promote uniform crimping and expansion of the frame.

Figure 29:
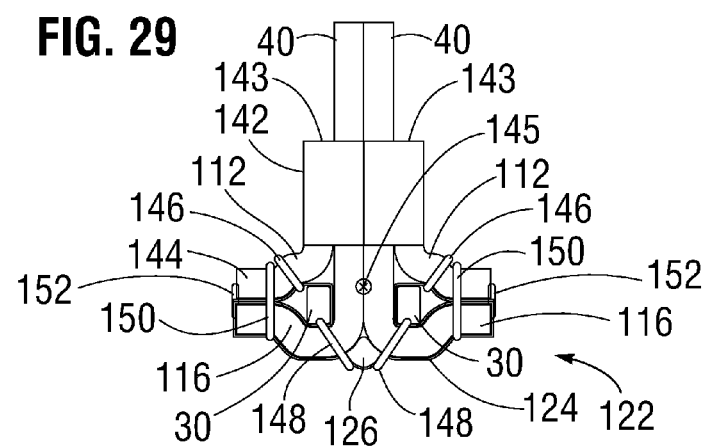
FIGS. 29-35 show the assembly of commissure portions of the leaflet structure with window frame portions of the frame.
Figure 30:
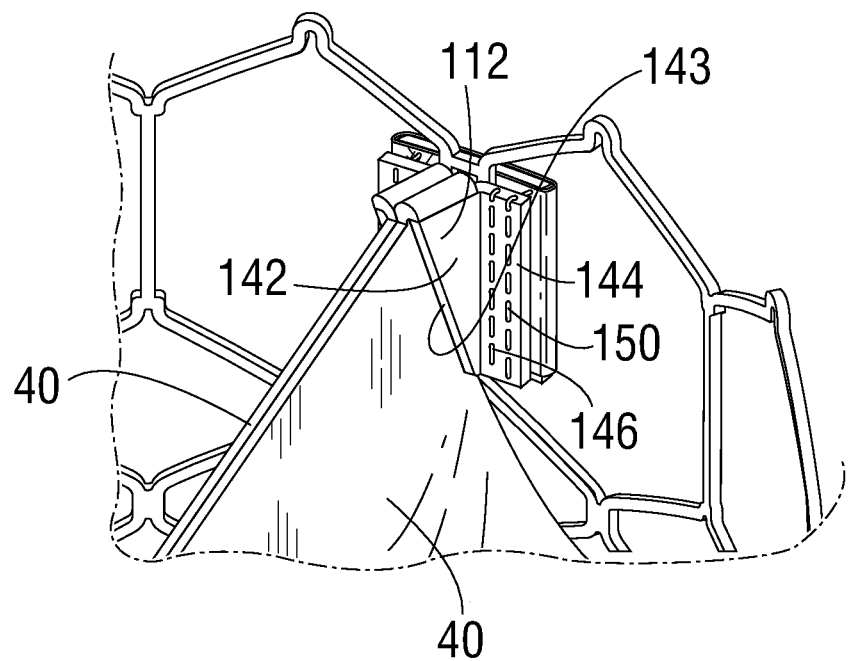
Figure 31:
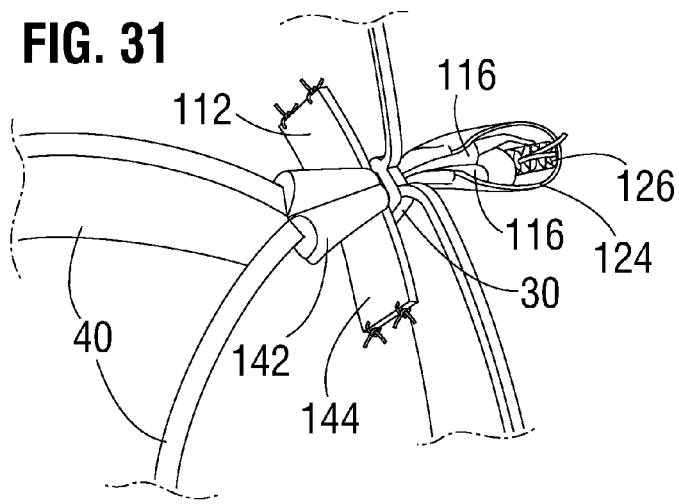
Figure 32:
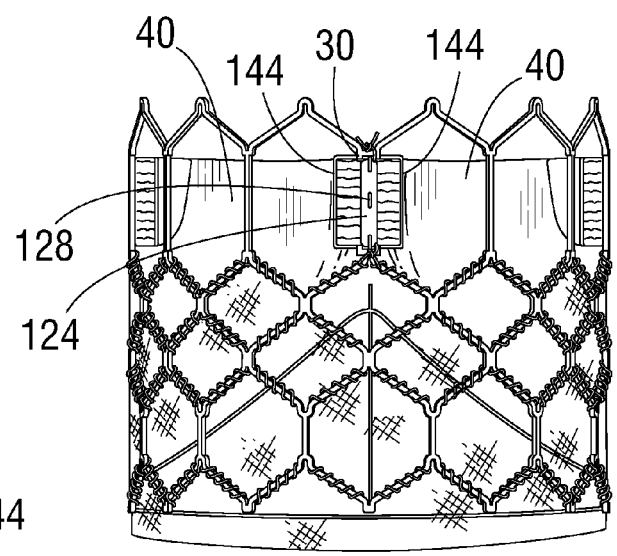

FIG. 29 is a cross-sectional view of a portion of the frame and leaflet structure showing the adjacent tab portions of two leaflets secured to a corresponding window frame portion 30. FIGS. 30-36 show one specific approach for securing the commissure portions 122 of the leaflet structure 14 to the commissure window frame portions 30 of the frame. First, as shown in FIG. 30, the flexible connector 124 securing two adjacent sides of two leaflets is folded widthwise and the upper tab portions 112 are folded downwardly against the flexible connector. As best shown in FIGS. 30 and 31, each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, as shown in FIG. 31, the commissure tab assembly (comprised of a pair of lower tab portions 116 connected by connector 124) is inserted through the commissure window 20 of a corresponding window frame portion 30. FIG. 32 is a side view of the frame 12 showing the commissure tab assembly extending outwardly through the window frame portion 30.

Figure 33:
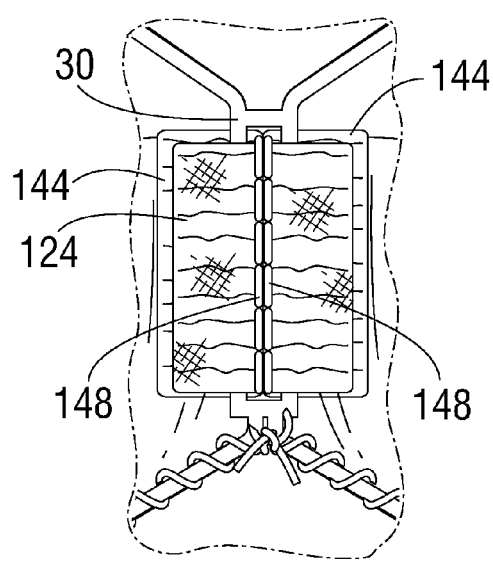
Figure 34:
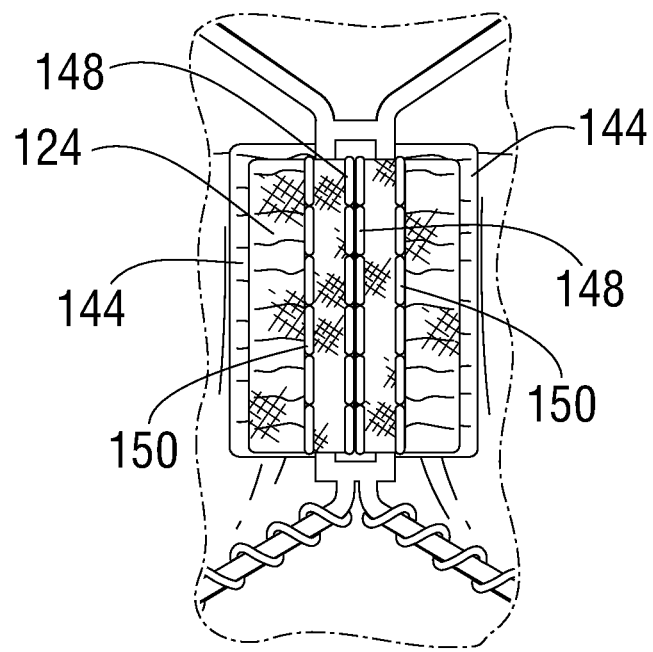
Figure 35:
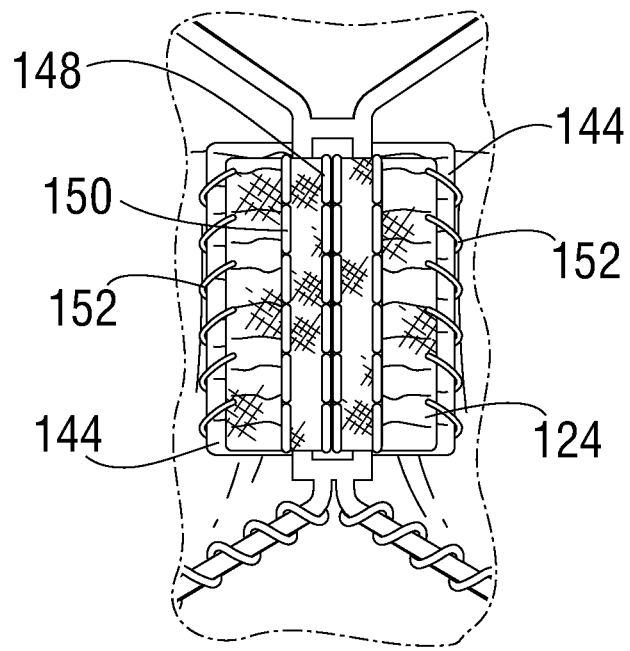

As best shown in FIGS. 29 and 33, the commissure tab assembly is pressed radially inwardly at the wedge 126 such that one of the lower tab portions 116 and a portion of the connector 124 is folded against the frame 12 on one side of the window frame portion 30 and the other lower tab portion 116 and a portion of the connector 124 is folded against the frame 12 on other side of the window frame portion 30. A pair of suture lines 148 are formed to retain the lower tab portions 116 against the frame 12 in the manner shown in FIG. 29. Each suture line 148 extends through connector 124, a lower tab portion 116, the wedge 126, and another portion of connector 124. Then, as shown in FIGS. 29 and 34, each lower tab portion 116 is secured to a corresponding upper tab portion 112 with a primary suture line 150 that extends through one layer of connector 124, the lower tab portion 116, another layer of connector 124, another layer of connector 124, and the upper tab portion 112. Finally, as shown in FIGS. 29 and 35, the suture material used to form the primary suture line 150 can be used to further form whip stitches 152 at the edges of the tab portions 112, 116 that extend through two layers of connector 124 sandwiched between tab portions 112, 116.

As shown in FIGS. 29 and 30, the folded down upper tab portions 112 form a double layer of leaflet material at the commissures. The inner portions 142 of the upper tab portions 112 are positioned flat abutting layers of the two leaflets 40 forming the commissures, such that each commissure comprises four layers of leaflet material just inside of the window frames 30. This four layered portion of the commissures can be more resistant to bending, or articulating, than the portion of the leaflets 40 just radially inward from the relatively more rigid four layered portion. This causes the leaflets 40 to articulate primarily at inner edges 143 of the folded-down inner portions 142 in response to blood flowing through the valve during operation within the body, as opposed to articulating about the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis 145 (FIG. 29) adjacent to the window frame 30, with each inner portion 142 folding out against the respective outer portion 144. For example, this can occur when the valve 10 is compressed and mounted onto a delivery shaft, allowing for a smaller crimped diameter. The four layered portion of the commissures can also splay apart about axis 145 when the balloon catheter is inflated during expansion of the valve, which can relieve some of the pressure on the commissures caused by the balloon and so the commissures are not damaged during expansion.

Figure 36:
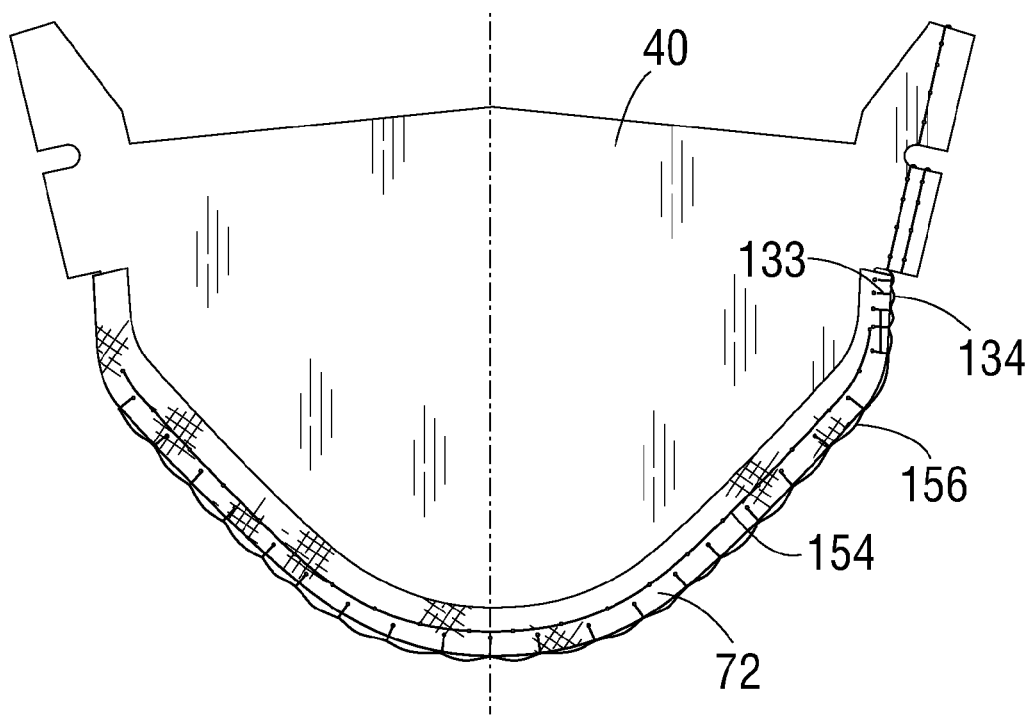
FIGS. 36-40 show the assembly of the leaflet structure with the inner skirt along a lower edge of the leaflets.
Figure 37:
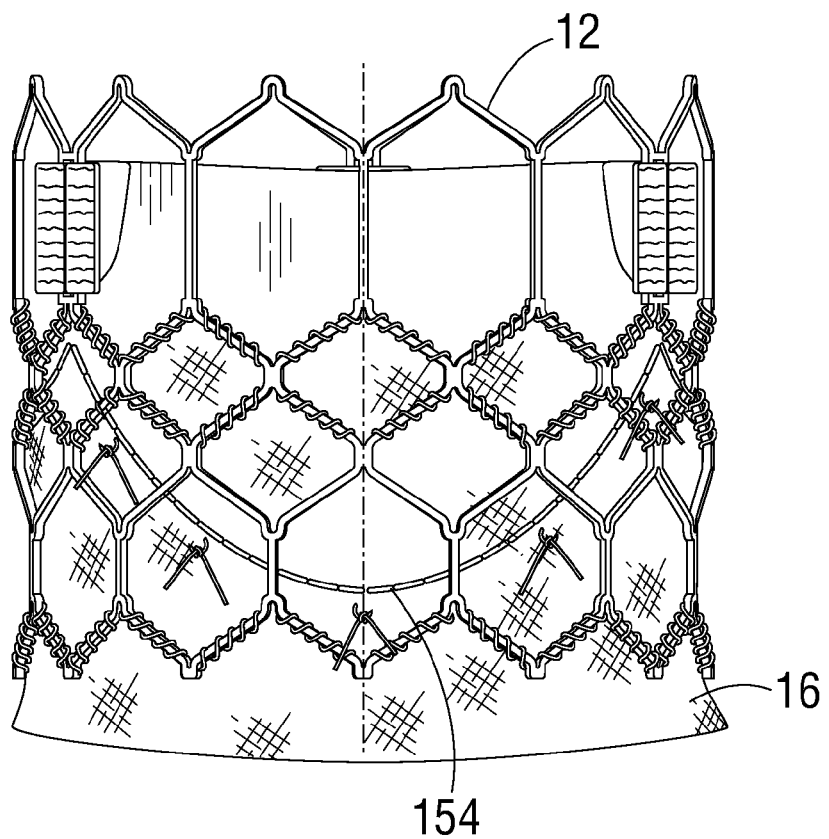
Figure 40:
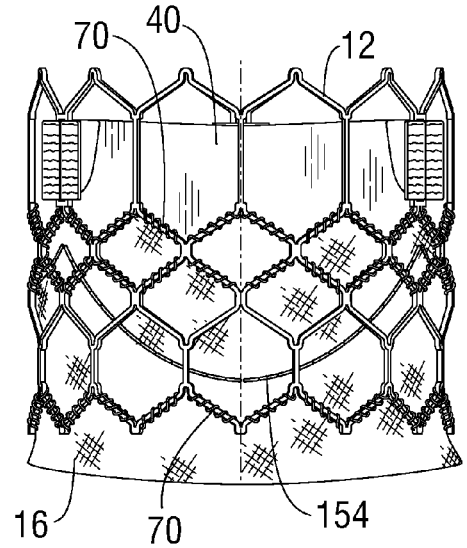

After all three commissure tab assemblies are secured to respective window frame portions 30, the lower edges of the leaflets 40 between the commissure tab assemblies can be sutured to the inner skirt 16. For example, as shown in FIGS. 36-38, each leaflet 40 can be sutured to the skirt 16 along suture line 154 using, for example, Ethibond thread. The sutures can be in-and-out sutures extending through each leaflet 40, the skirt 16 and each reinforcing strip 72. Each leaflet 40 and respective reinforcing strip 72 can be sewn separately to the skirt 16. In this manner, the lower edges of the leaflets are secured to the frame 12 via the skirt 16. As shown in FIG. 38, the leaflets can be further secured to the skirt with blanket sutures 156 that extend through each reinforcing strip 72, leaflet 40 and the skirt 16 while looping around the edges of the reinforcing strips 72 and leaflets 40. The sutures 156 can be formed from PTFE suture material. FIGS. 39 and 40 show the frame 12, leaflet structure 14 and the skirt 16 after securing the leaflet structure and the skirt to the frame and the leaflet structure to the skirt.

Figure 41:
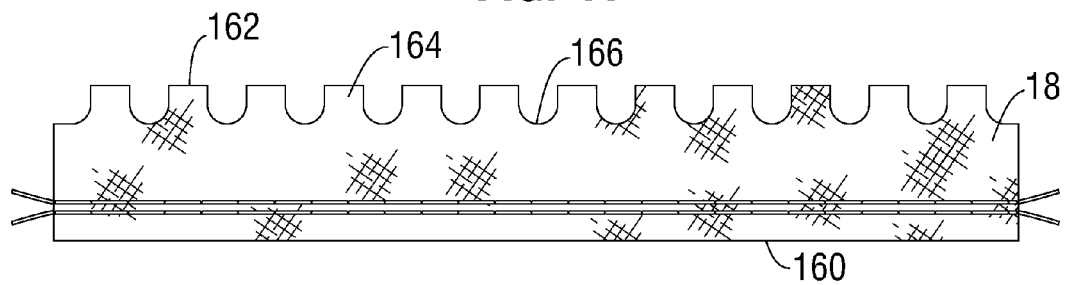
FIG. 41 shows an exemplary outer skirt laid out flat.

FIG. 41 shows a flattened view of the outer skirt 18 prior to its attachment to the frame 12. The outer skirt 18 can be laser cut or otherwise formed from a strong, durable piece of material, such as woven PET, although other synthetic or natural materials can be used. The outer skirt 18 can have a substantially straight lower edge 160 and an upper edge 162 defining a plurality of alternating projections 164 and notches 166. As best shown in FIG. 42, the lower edge 160 of the skirt 18 can be sutured to the lower edge of the inner skirt 16 at the inflow end of the valve. As shown in FIG. 43, each projection 164 can be sutured to the second rung II of struts 24 of the frame 12. The corners 162 of the projections 164 can be folded over respective struts of rung II and secured with sutures 168.

As can be seen in FIGS. 1, 3 and 43, the outer skirt 18 is secured to the frame 12 such that when the frame is in its expanded state, there is excess material or slack between the outer skirt's lower and upper edges 160, 162 that does not lie flat against the outer surface of the frame 12. In other words, the outer skirt is configured with excess material which causes the outer skirt to bulge outwardly as the frame foreshortens (i.e., shortens in length) during radial expansion. Accordingly, when the valve 10 is deployed within the body, the excess material of the outer skirt 18 can fill in gaps between the frame 12 and the surrounding native annulus to assist in forming a good fluid-tight seal between the valve and the native annulus. The outer skirt 18 therefore cooperates with the inner skirt 16 to avoid perivalvular leakage after implantation of the valve 10. In another advantageous feature, the slack between the lower and upper edges of the outer skirt 18 allows the frame 12 to elongate axially during crimping without any resistance from the outer skirt and the outer skirt does not substantially affect the outer diameter of the prosthetic valve in the crimped condition.

FIG. 56 shows the valve 10 of FIGS. 1-3 and 42-43 mounted on an elongated shaft 180 of a delivery apparatus, forming a delivery assembly for implanting the valve 10 in a patient's body. The valve 10 is mounted in a radially collapsed configuration for delivery into the body. The shaft 180 comprises an inflatable balloon 182 for expanding the balloon within the body, the crimped valve 10 being positioned over the deflated balloon. The frame 12 of the valve 10, when in the radially compressed, mounted configuration, comprises an inflow end portion 174 (see FIG. 54) that has an outer diameter $D_2$ that is smaller than the outer diameter $D_1$ of the outflow end portion of the frame. The tapering of the frame can be at least partially due to the V-shaped leaflets 40, as the V-shaped leaflets have less leaflet material within the inflow end portion of the frame 12 compared to a more rounded, U-shaped leaflet. Due to the tapered shape of the frame 12 in the mounted state, even with the additional thickness of the outer skirt 18 positioned around the inflow end portion 174 of the frame 12 the overall outer diameter of the inflow end portion of the valve 10 can be about equal to, or less than, the overall outer diameter of the outflow end portion of the valve.

Furthermore, as shown in FIG. 56, the valve 10 comprises commissure portions of the leaflets extending radially outwardly through corresponding window frame portion 30 to locations outside of the frame and sutured to the side struts of the commissure window frame. To minimize the crimp profile of the valve, the window frame portions 30 can be depressed radially inwardly relative to the surrounding portions of the frame, such as the frame portions extending between adjacent commissure windows, when the valve is radially compressed to the collapsed configuration on the shaft. For example, the commissure windows 30 of the frame can be depressed inwardly a radial distance of between 0.2 mm and 1.0 mm relative to the portions of the frame extending between adjacent commissure windows when the valve is radially collapsed. In this way, the outer diameter of the outflow end portion the valve comprising the commissure portions can be generally consistent, as opposed to the commissure portions jutting outward from the surrounding portions of the valve, which could hinder delivery of the valve into the body. Even with the radially depressed commissure window frames 30, the outer diameter of the inflow end portion of the frame can still be smaller than, or about equal to, the outer diameter of the outflow end portion of the frame when the valve is radially collapsed on the shaft, allowing for a minimal maximum overall diameter of the valve. By minimizing the diameter of the valve when mounted on the delivery shaft, the assembly can contained within a smaller diameter catheter and thus can be passed through smaller vessels in the body and can be less invasive in general.

Figure 44:
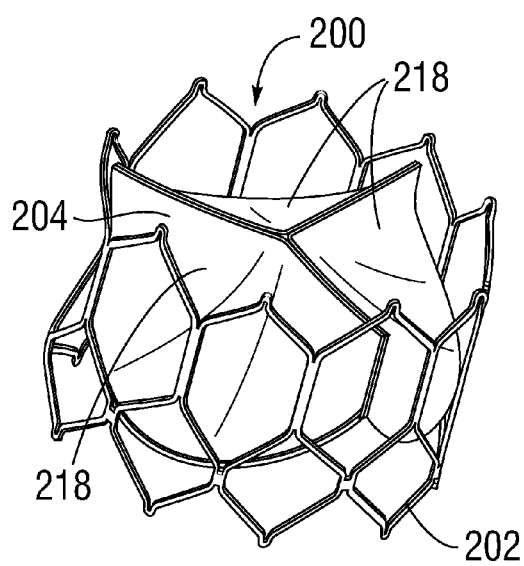
FIGS. 44-48 show an alternative embodiment of a prosthetic heart valve.

FIG. 44 illustrates a prosthetic heart valve 200, according to another embodiment. The heart valve 200 includes a frame, or stent, 202 and a leaflet structure 204 mounted on the stent.

The leaflet structure 204 can include a plurality of leaflets 218 (e.g., three, as depicted), which can be sutured to each other and to the frame 202 using suitable techniques and/or mechanisms. The frame 202 can be adapted to include commissure frame portions 30 (as shown in FIG. 4) to assist in suturing the leaflets to the frame.

Figure 45:
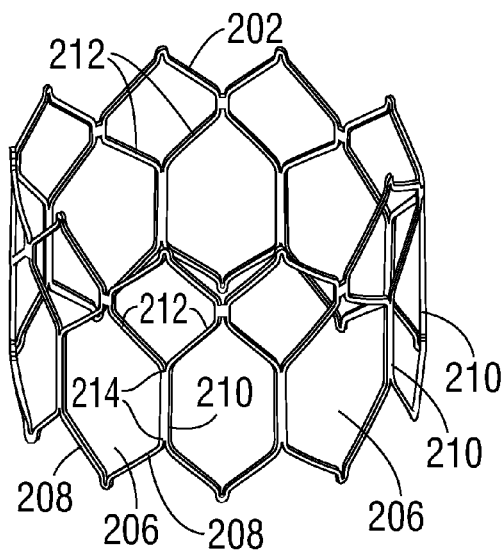
Figure 46:
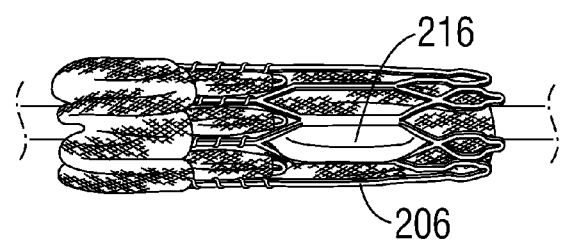
Figure 47:
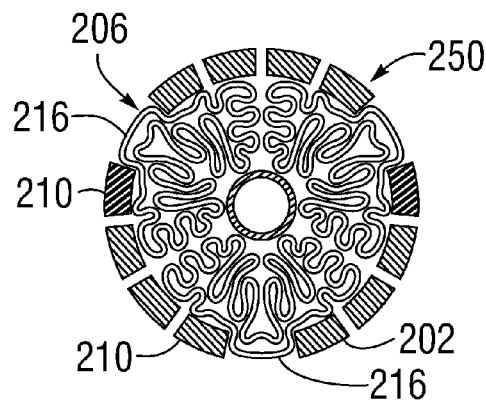

The frame 202 shares some design features of the frame 12 described above. In particular, like frame 12, the frame 202 has relatively large frame openings 206 along the area of the frame that supports the leaflet structure, as shown in FIG. 45. The openings 206 are defined by a row of angled struts 208 at the outflow end of the frame, a plurality of axially extending, circumferentially spaced struts 210, and an intermediate row of angled struts 212. As shown, the axial struts 210 desirably are thinner than the junctions 214 connecting the opposite ends of the axial struts 210 to the convergence of two struts 212 and to the convergence of two struts 208. By virtue of this configuration, the width of openings 206 remain large enough when the valve is radially compressed to a delivery configuration to allow portions of the leaflet structure 204 to protrude outwardly through the openings, as indicated at 216 in FIGS. 46 and 47. This allows the valve to be crimped to a relatively smaller diameter than if all of the leaflet material is constrained within the crimped frame.

Figure 48:
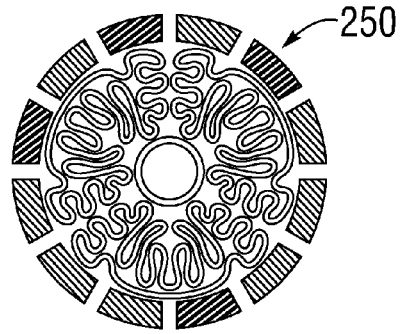

For purposes of comparison, FIG. 48 is a cross section of a known prosthetic valve 250 showing the valve in its crimped state. When the valve is radially compressed, the spacing between adjacent struts is relatively small and does not allow portions of the leaflet structure to protrude outwardly through the frame. Consequently, the presence of all of the leaflet material being constrained within the inside of the frame limits the crimping diameter of the valve.

Figure 49:
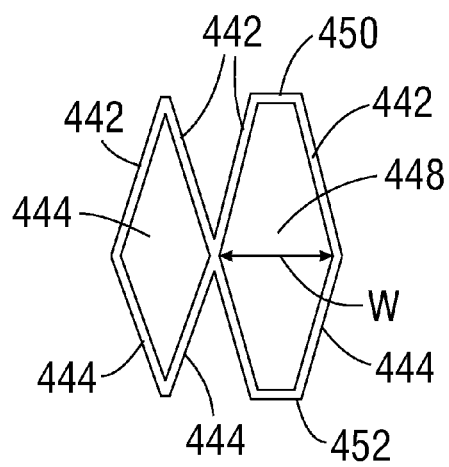
FIGS. 49-52 show portions of an alternative embodiment of a frame.
Figure 50:
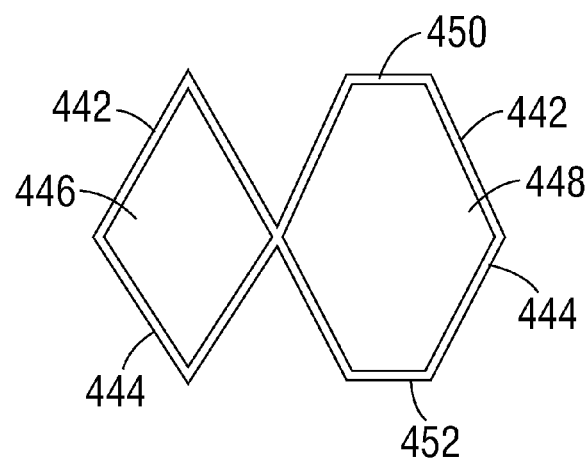

FIGS. 49 and 50 show a flattened section of an alternative frame construction that can allow portions of the leaflets to protrude outwardly through the frame in the crimped state. This frame construction can be implemented in the valve 10 described above. FIG. 49 shows the frame section in the radially compressed state while FIG. 50 shows the frame section in the radially expanded state. The frame (only a portion of which is shown) includes a first, circumferentially extending row of angled struts 442 and at least a second, circumferentially extending row of angled struts 444. Some openings in the frame are diamond shaped openings 446 formed by adjacent struts 442 connected to each other at their upper ends and adjacent struts 444 connected to each other at their lower ends. The frame also includes larger openings 448 that are formed by adjacent struts 442 connected at their upper ends to respective ends of a horizontal strut 450 and by adjacent struts 444 connected at their lower ends to respective ends of a horizontal strut 452. When the frame is radially compressed, the horizontal struts 450, 452 maintains the width W of openings 448 large enough to permit portions of the valve's leaflets to protrude outwardly through the frame. Thus, the width of openings 448 is greater than the width of openings 446 when the frame is crimped. The frame can be formed with openings 446, 448 alternating around the circumference of the frame. Alternatively, openings 448 can be located at selected positions along the frame's length and circumference to correspond to areas where the leaflet material tend to bunch up within the frame, such as between the commissures.

Figure 51:
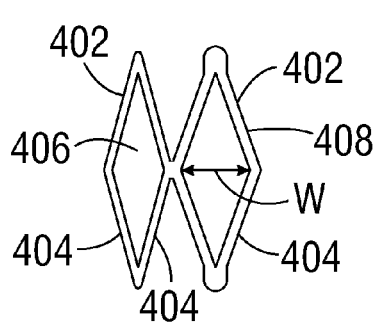
Figure 52:
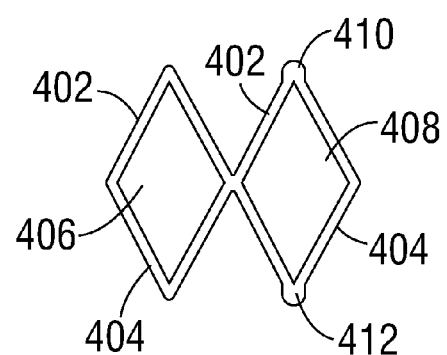

FIGS. 51 and 52 show a flattened section of another frame construction that can allow portions of the leaflets to protrude outwardly through the frame in the crimped state. This frame construction can be implemented in the valve 10 described above. FIG. 51 shows the frame section in the radially compressed state while FIG. 52 shows the frame section in the radially expanded state. The frame (only a portion of which is shown) includes a first, circumferentially extending row of angled struts 402 and at least a second, circumferentially extending row of angled struts 404. Some openings in the frame are diamond shaped openings 406 formed by adjacent struts 402 connected to each other at their upper ends and adjacent struts 404 connected to each other at their lower ends. The frame also includes openings 408 that are formed by adjacent struts 402 connected at their upper ends to an enlarged node or junction 410 and by adjacent struts 404 connected at their lower ends to an enlarged node or junction 412. The junctions 410, 412 add rigidity to the frame at those locations such that when the frame is radially compressed, the width W of openings 408 remains large enough to permit portions of the valve's leaflets to protrude outwardly through the frame. Thus, the width of openings 408 is greater than the width of openings 406 when the frame is crimped. The frame can be formed with openings 406, 408 alternating around the circumference of the frame. Alternatively, openings 408 can be located at selected positions along the frame's length and circumference to correspond to areas where the leaflet material tend to bunch up within the frame, such as between the commissures.

Figure 57:
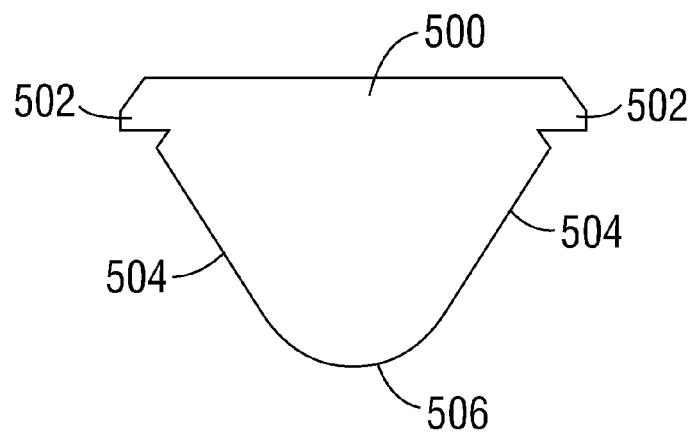
FIGS. 57 and 58 shows an embodiment of a leaflet have a generally V-shaped configuration.
Figure 58:
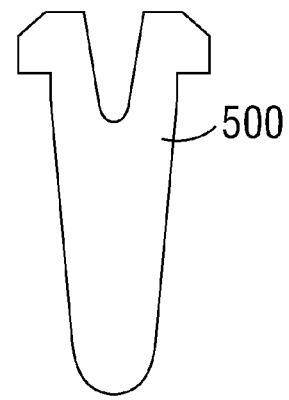

FIG. 57 shows a leaflet 500 for a prosthetic valve (e.g., valve 10 or 200), according to another embodiment. The leaflet 500 has an overall V-shape, similar to leaflets 40 described above. The leaflet 500 has two tab portions 502 on opposite sides of the leaflets which are secured to adjacent tab portions of other leaflets to form the commissures of the leaflet structure. The sub-commissure portion of the leaflet 500 (the portion below the tabs 502) include two substantially straight edges 504 that extend from respective locations just below the tabs 502 to a curved lower edge 506. FIG. 58 shows the general shape of the leaflet 500 when the valve is crimped. The frame (not shown in FIGS. 57-58) slightly elongates when crimped, causing the leaflet 500 to become slightly elongated.

The tapered profile of the sub-commissure portion of the leaflet reduces the amount of leaflet material in the lower half of the crimped valve to minimize the crimp diameter of that portion of the valve. Thus, if additional components are mounted to that portion of the valve, such as an outer skirt 18, the reduced profile of that portion of the valve can help offset or minimize the increase in diameter caused by the additional component. Additionally, the commissure tabs 502 are relatively short and require less sutures for forming the commissures of the leaflet structure than known leaflet designs (such as T-shaped and scalloped leaflets), which better distributes and reduces the bulkiness of the leaflet material when the valve is crimped.

Figure 59:
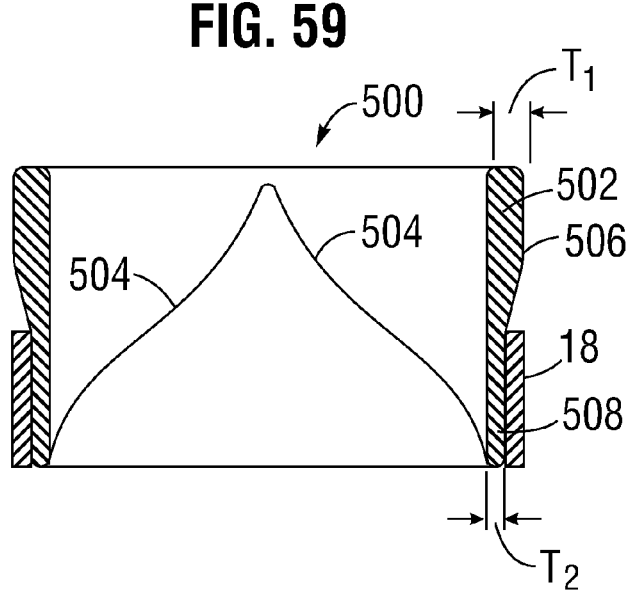
FIG. 59 shows a cross-sectional view of an alternative embodiment of a prosthetic valve having a variable thickness frame.

FIG. 59 shows a cross-sectional view of a valve 500, according to another embodiment. The valve 500 comprises a frame 502, leaflets 504, and an outer skirt 18 mounted (e.g., by sutures) to the outer surface of the frame 502. The frame 502 has a thickness that varies along its length to optimize strength where needed, yet minimize material (and therefore crimp profile) at selected regions of the frame. In the embodiment shown, the outflow end portion 506 of the frame has a maximum thickness $T_1$ (measured from the inside diameter to the outside diameter of that portion of the frame) and the inflow end portion 508 of the frame has a minimum thickness $T_2$ (measured from the inside diameter to the outside diameter of that portion of the frame). It should be noted that the struts of the frame 502 (which are not shown in FIG. 59) that form the outflow end portion 506 have a thickness $T_1$ and the struts that form the inflow end portion 508 have a thickness $T_2$. The frame 502 can have an identical construction to the frame 12 described above, except for the variable thickness of the frame. The areas of reduced thickness can be formed using a variety of manufacturing techniques, such as electro-polishing selected portions of the frame (the non-polished portions can be masked), grinding selected portions of the frame, wire cutting, or other suitable techniques.

The outflow end portion 502 generally corresponds to the region of the frame that supports the commissures of the leaflets 504 and typically experiences the greatest loading on the valve. Therefore the outflow end portion 502 of the frame has a greater thickness $T_1$ selected to provide the required strength under anticipated loads. The inflow end portion 508 supports an additional layer of material by virtue of the outer skirt 18. The reduced thickness of the inflow end portion 508 allows the inflow end portion to be crimped to a smaller diameter than the outflow end portion. This offsets or minimizes the increase in the crimp diameter caused by the addition of the outer skirt 18.

FIGS. 60-62 show an another embodiment of an implantable prosthetic valve 310 that comprises a leaflet structure 314 and a radially collapsible and expandable frame 312 (similar to the frame 50 shown in FIG. 11) having a plurality of radially spaced commissure windows 318 that are used to secure the leaflet structure within the frame. The valve 310 also comprises a skirt 316 secured between the inner surface of the frame 312 and the curved lower edges 364 of the leaflet structure 314. The valve 310 has a lower, inflow end 340 and an upper, outflow end 342.

Figure 63:
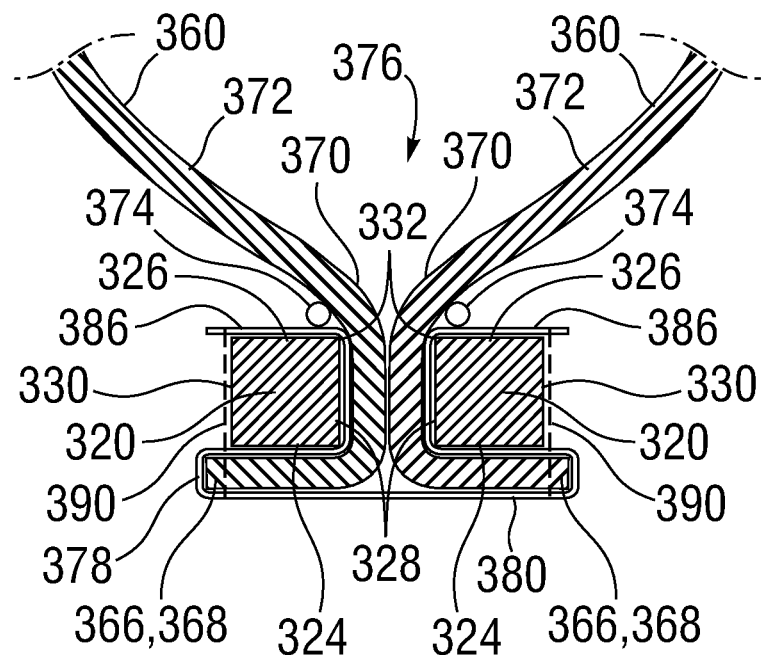
FIGS. 63-71 are cross-sectional views of a commissure of the valve of FIG. 61 showing various techniques for suturing a pair of leaflet side tabs to a commissure window using a reinforcing sheet.

As shown in FIG. 60A, each window 318 comprises an enclosed opening 334 between two axially extending side struts 320, respectively. Each side strut comprises a generally rectangular, e.g. square, cross-sectional profile, as shown in FIG. 63. Each rectangular side strut 320 comprises four surfaces: an exterior surface 324 on a radially outward facing side, and interior surface 326 on a radially inward facing side, a medial surface 328 on a side facing the other side strut, and a lateral surface 330 on a side facing away from the other side strut. In other embodiments, side struts can comprise other cross-sectional shapes, such circular or hexagonal.

The leaflet structure comprises a plurality of leaflets 360, each comprising a pair of side tabs 366 secured to the frame 312, a curved lower edge 364 secured to the skirt 316, and an articulation portion 372 between the side tabs and the lower edge. Each side tab 366 is paired with an adjacent side tab of another leaflet 360 to form commissures 376 of the leaflet structure 314. Each pair of side tabs 366 extends radially outwardly through a corresponding commissure window 318 to a location outside of the frame 312 and is secured to the side struts 320 of the window, such as with sutures, as shown in FIG. 62. In some embodiments, each side tab 366 comprises an end portion 368 (see FIG. 64) and the two side tab end portions 368 of each commissure 376 extend circumferentially away from one another and along the exterior surfaces 324 of respective side struts 320 of the window 318.

In some embodiments, each commissure 376 further comprises at least one non-rigid reinforcing sheet 378 sutured to the side tabs 366 and to the side struts 320. The sheets 378 can comprise a flexible, tear resistant material, including a variety of natural and/or synthetic biocompatible materials. Exemplary synthetic materials can include polymers such as nylon, silicone, and polyesters, including PET. In one example, the sheets 378 comprise a woven PET fabric.

Figure 64:
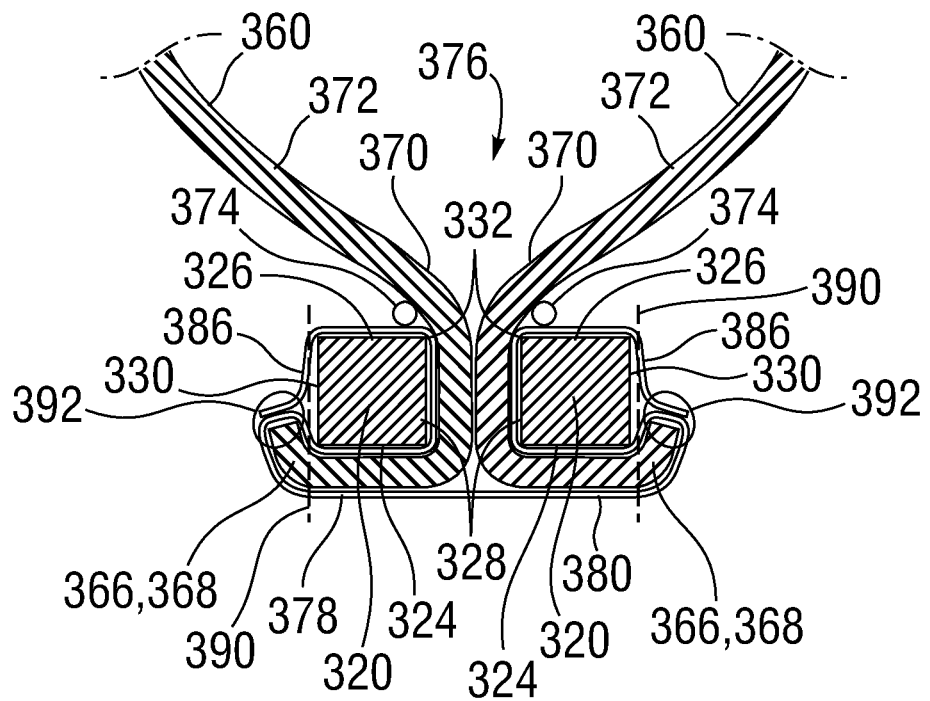

Each reinforcing sheet 378 can be generally rectangular (when laid flat) and can comprise a middle portion 380 and opposing end portions 386. In some embodiments, a first end portion 386 of the sheet is secured to a first side strut 320 and a second end portion 386 of the sheet is secured to the second side strut 320, as shown in FIG. 64. The sheet 378 separates the side tabs 366 from the side struts 320 such that side tabs do not contact the side struts. For example, each end portion 386 of the sheet can be wrapped completely around a respective side strut 320, as shown in FIG. 64.

The side tabs 366 and the reinforcing sheet 378 can be secured to the side struts 320 in multiple stages. For example, FIG. 63 shows an exemplary first suturing stage wherein the sheet is positioned such that the middle portion 380 of the sheet extends circumferentially across outer surfaces of the end portions 368 of the side tabs 366 and each end portion 386 of the sheet extends between a respective side tab 366 and the exterior, medial and interior surfaces 324, 328, 326, respectively, of a respective side strut 320. The sheet 378 surrounds the side tabs 366 and protects the side tabs from edges of the side struts 320. A pair of in-and-out sutures 390 can secure each side tab 366 and one end of the sheet 378 to a respective strut 320. As shown in FIG. 63, each suture 390 can be oriented generally perpendicularly to the circumference of the frame 312 along the lateral surfaces 330 of the side struts 320 and can pass radially back and forth through the commissure 376 at a plurality of difference longitudinal positions. Each suture 390 can intersect a first layer of the sheet 378, a side tab end portion 368, a second layer of the sheet, and a third layer of the sheet, in that order moving radially inward. The sutures 390 secure the sheet 378 to the side tab end portions 368 and tighten the sheet end portions 386 around the side struts 320, thereby securing the side tabs 366 to the side struts 320 and securing the leaflet structure 314 to the frame 312.

FIG. 64 shows an exemplary second suturing stage wherein a second pair of sutures 392 are used to tie down loose portions of the reinforcing sheet 378. For example, the second sutures 392 can intersect the portions of the middle portion 380 and the end portions 386 of the sheet that extend laterally beyond the first sutures 390. The second sutures 392 can be helical whip stitches that intersect the commissures 376 at a plurality of different longitudinal positions, as shown in FIG. 62, and secure the loose portions of the sheet 378 tightly against the lateral surfaces 330 of the side struts.

Both the first sutures 390 and the second sutures 392 can be positioned adjacent to the lateral surfaces 330 of the struts 320 and spaced away from the window opening 334. This placement of the sutures can reduce the stress on the sutures caused by movement of the articulation portions 372 of the leaflets. Instead, much of this stress is transferred from flex hinges 370 of the leaflets to the side struts 320 near interior-medial edges 332 of the struts.

The reinforcing sheet 378 protects the flex hinges 370 from damage caused by the interior-medial edges 332 of the struts 320 as the leaflets articulate between open and closed positions, as shown in FIG. 64. In addition, some embodiments can also include longitudinally extending cushion strips 374 positioned between the flex hinges 370 and the struts 320, such as adjacent to the interior-medial edges 332, as shown in FIG. 64, to further protect the flex hinges from damage caused by the struts. The cushion strips 374 can comprise a flexible, compressible material, such as PET fabric, pericardial tissue, or various other biocompatible materials. In some embodiments, the cushion strips can comprise a tube filled with a resilient material. For example, the cushion strip can comprise a PET tube filled with pericardial tissue. In other embodiments, the outer tubular covering of the cushion strips can be formed from sheet 378 and can be filled with a resilient material. The sheet can be secured around the resilient material with sutures to retain the cushioning strips properly located as shown in FIG. 64. In other embodiments, separate cushion strips 374 can be sutured to the reinforcing sheet 378. The cushion strips 374 can have a thickness similar to the bars 62 to provide a radial clearance between the side struts 320 and the articulating portions 372 of the leaflets to prevent or minimize contact between the leaflets and the inner surface of the frame during the cardiac cycle.

Figure 65:
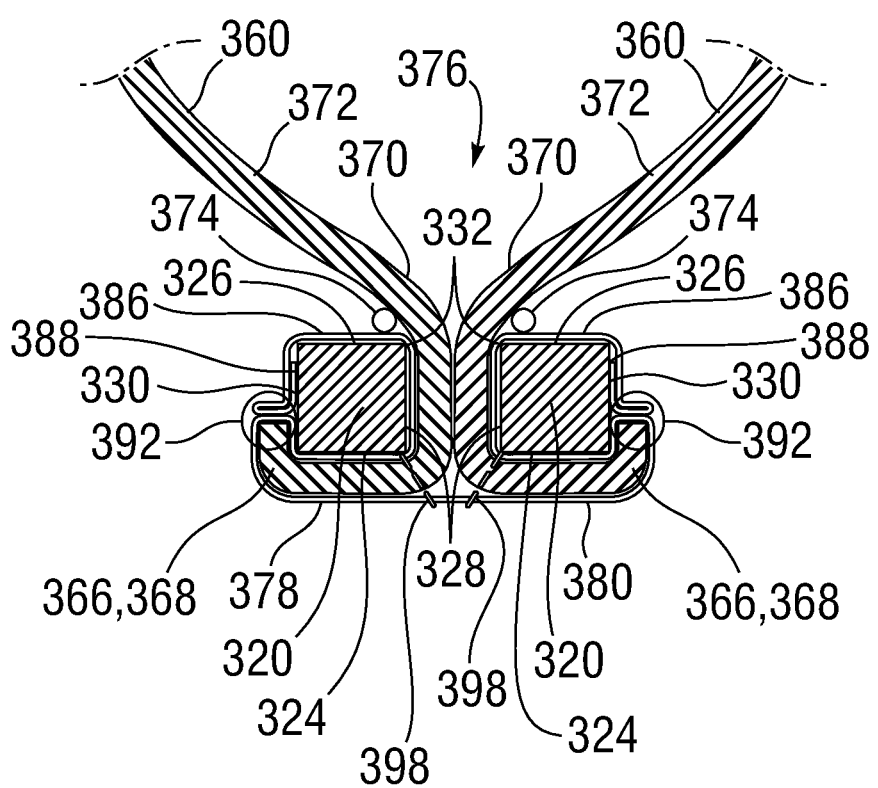

FIG. 65 shows an embodiment similar to FIGS. 63 and 64 but with a different suturing pattern. In FIG. 65, the sutures 390 are replaced with sutures 398 that secure the sheet 378 around the end portions 368 of the side tabs. Each suture 398 intersects the middle portion 380 of the sheet, one of the side tabs 366, and a second layer of the sheet adjacent to the medial-exterior edge 324 of each side strut. The sutures 398 can comprise in-and-out stitches that intersect the commissures at a plurality of different longitudinal positions. Each end portion of the sheet 378 can comprise a folded portion 388 that is folded under to form a double layer of the sheet 378 along the surface of the respective side strut 320. The sutures 392 secure the end portions 386 of the sheet and the end portions 368 of the side tabs tightly around the lateral surfaces 330 of the side struts.

Figure 66:
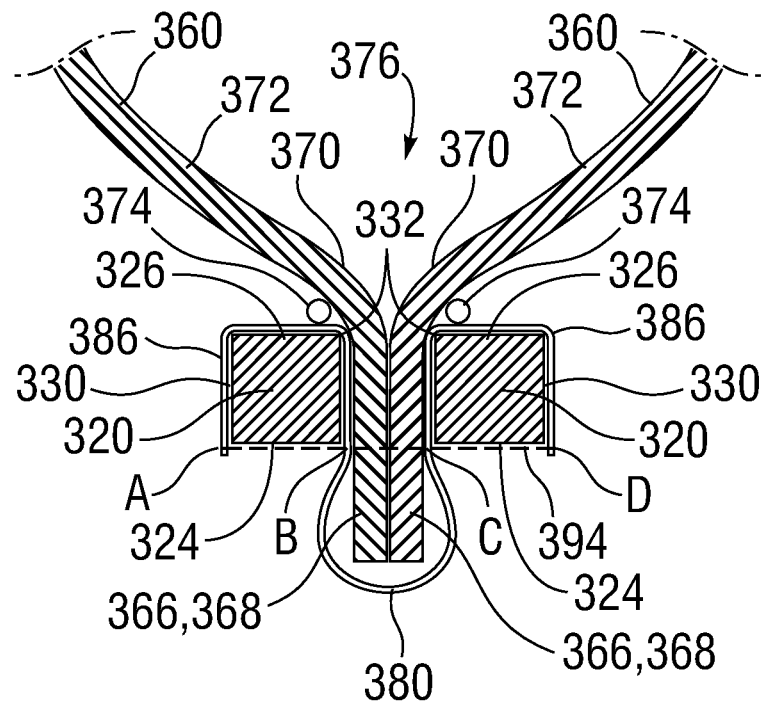
Figure 67:
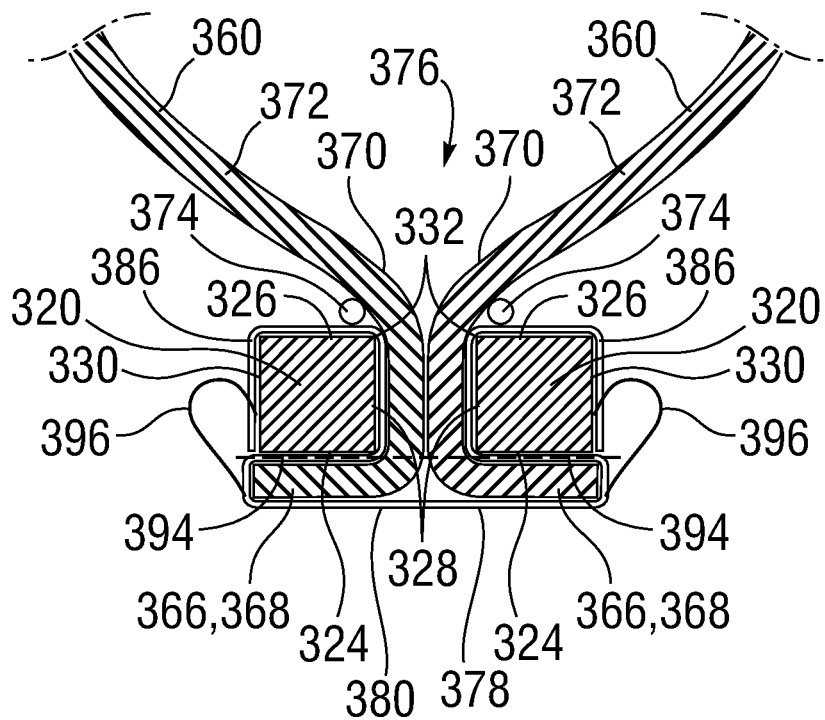

FIGS. 66 and 67 show an alternative method for suturing the side tabs 366 and the sheet 378 to the side struts 320. FIG. 66 shows suture line 394 positioned along the exterior surfaces 324 of the side struts and generally perpendicular to the radius of the frame. The suture 394 intersects both side tabs 366 and both end portions 386 of the sheet 378. The suture 394 secures each end portion 386 of the sheet tightly around the medial, interior, and lateral surfaces 328, 326, 330, respectively, of the respective side strut 320, and also secures the middle portion 380 of the sheet loosely around the end portions 368 of the side tabs 366. In the embodiment shown in FIG. 66, the suture 394 intersects a first sheet layer A, a second sheet layer B, the two side tabs 366, a third sheet layer C, and a fourth sheet layer D, in that order.

After the first suture 394 is in place, the end portions 368 of the side tabs are spread apart and positioned adjacent to the exterior surfaces 324 of the side struts 320, as shown in FIG. 67. This tightens the loose middle portion 380 of the sheet around the end portions 368 of the side tabs. A pair of sutures 396 can then secure the middle portion 380 of the sheet tightly to the end portions 386 of the sheet to hold the end portions 368 of the side tabs in place, as shown in FIG. 67. The sutures 396 can be looping whip stitches that intersect the commissure 376 at a plurality of different longitudinal positions, similar to the sutures 392 in FIG. 64.

Figure 68:
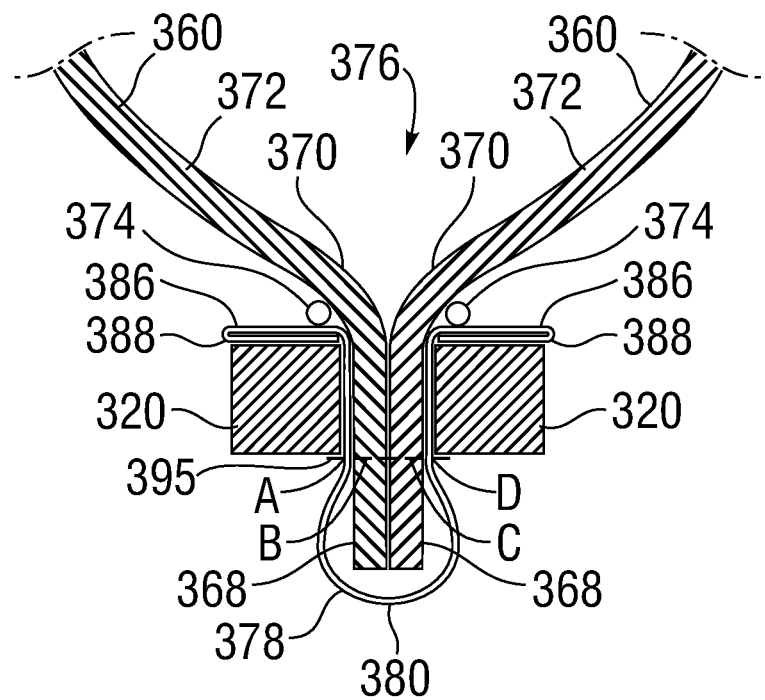
Figure 69:
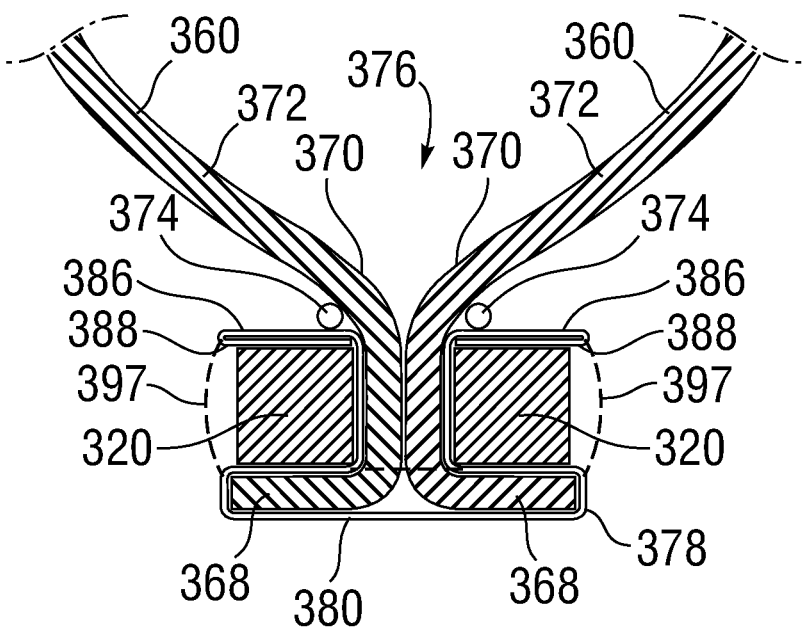

FIGS. 68 and 69 show another alternative method for suturing the side tabs 366 and the sheet 378 to the side struts 320. FIG. 68 shows a suture line 395 positioned along the exterior side of the window opening and oriented generally perpendicular to the radius of the frame. The suture 395 intersects both side tabs 366 and two portions of the sheet 378. The suture 395 secures the middle portion 380 of the sheet which extends loosely around the end portions 368 of the side tabs 366. In the embodiment shown in FIG. 68, the suture 395 intersects a first sheet layer A, a first side tab B, a second side tab C, and a second sheet layer D, in that order.

After the first suture 395 is in place, the end portions 368 of the side tabs are spread apart and positioned adjacent to the exterior surfaces 324 of the side struts 320, as shown in FIG. 69. This tightens the loose middle portion 380 of the sheet around the end portions 368 of the side tabs. A pair of sutures 397 can then secure the middle portion 380 of the sheet tightly to the end portions 386 of the sheet to hold the end portions 368 of the side tabs in place, as shown in FIG. 69. The end portions 386 of the sheet can comprise a folded under portion 388, creating a double layer of sheet material to reinforce the sutures 397. The sutures 397 can be looping whip stitches that intersect the commissure 376 at a plurality of different longitudinal positions, similar to the sutures 392 in FIG. 62.

Figure 70:
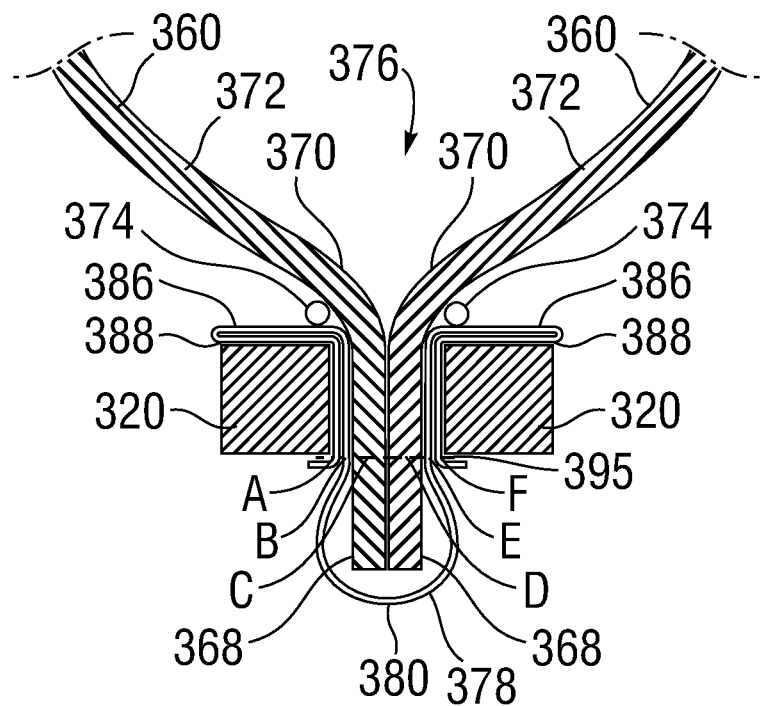
Figure 71:
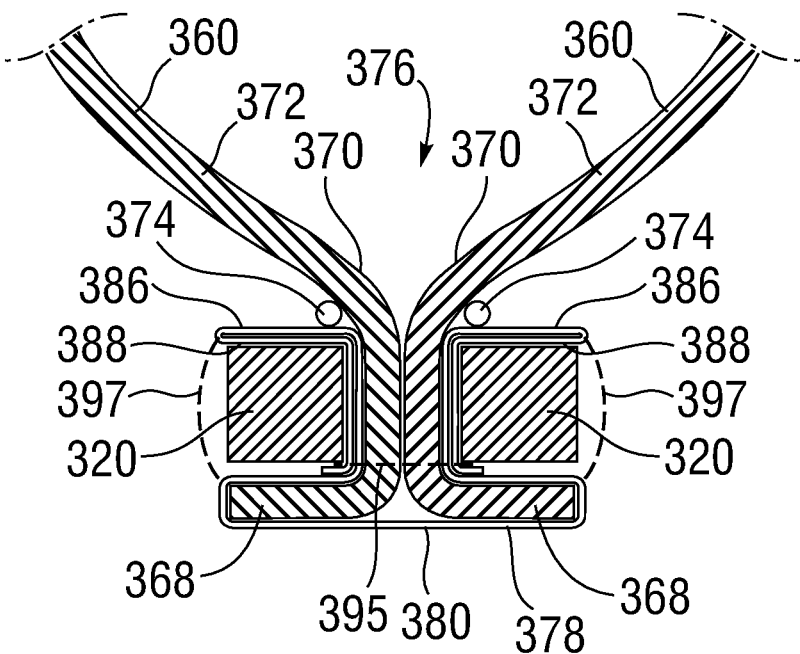

FIGS. 70 and 71 show yet another alternative method for suturing the side tabs 366 and the sheet 378 to the side struts 320. FIG. 70 shows the suture line 395 positioned along the exterior side of the window opening and oriented generally perpendicular to the radius of the frame. The suture 395 intersects both side tabs 366 and four portions or layers of the sheet 378. Each end portion 386 of the sheet comprises a folded portion 388 that forms a double layer of sheet material between the side tabs 366 and the medial surfaces 328 of the side struts. The suture 395 secures the middle portion 380 of the sheet loosely around the end portions 368 of the side tabs 366. As shown in FIG. 70, each stitch of the suture 395 intersects a first pair of sheet layers comprising layers A and B, a first side tab C, a second side tab D, and a second pair of sheet layers comprising layers E and F, in that order.

After the first suture 395 is in place, the end portions 368 of the side tabs are spread apart and positioned adjacent to the exterior surfaces 324 of the side struts 320, as shown in FIG. 71. This tightens the middle portion 380 of the sheet around the end portions 368 of the side tabs. A pair of sutures 397 can then secure the middle portion 380 of the sheet tightly to the end portions 386 of the sheet to hold the end portions 368 of the side tabs in place, as shown in FIG. 71. The folded portions 388 of the sheet create a double layer of sheet material to reinforce the sutures 397. The sutures 397 can be looping whip stitches that intersect the commissure 376 at a plurality of different longitudinal positions, similar to the sutures 392 in FIG. 62.

The commissure various configurations for attaching the leaflet structure 314 to the window frames 318 shown in FIGS. 61-71 can also be used as alternative ways to attach the leaflet structure 14 of the valve 10 of FIGS. 1-3 to the window frame portions 30 of frame 12.

FIGS. 72-74 show a prosthetic heart valve assembly 600 comprising an embodiment of a frame 602 for a prosthetic valve mounted on a balloon 606 of a delivery shaft 604. The frame 602 can be similar in shape to the frame 12 and can comprise in inflow end portion 610, an outflow end portion 612 and an intermediate portion 614. For clarity, the other components of the valve, such as the leaflets and the skirts, are not shown. The frame 602 can have a reduced thickness at the inflow end portion 610 and at the outflow end portion 612, relative to the thickness of the intermediate portion 614. Due to the thinner end portions, when the balloon 606 is inflated the end portions 610, 612 offer less resistance to expansion and expand faster than the intermediate portion 614, as shown in FIG. 73. Because the end portions expand faster than the intermediate portion, the frame 602 becomes confined on the balloon 606, inhibiting the frame from sliding towards either end of the balloon and reducing the risk of the frame sliding off the balloon prematurely. As shown in FIG. 74, further inflation of the balloon can cause the intermediate portion 614 of the frame to expand to the same final diameter as the end portions 610, 612 for implantation, after which the balloon can be deflated and removed. Controlling the position of the valve on the balloon can be important during delivery, especially with frames that foreshorten during expansion and move relative to the balloon. In the embodiment shown in FIGS. 72-74, the intermediate portion 614 of the frame can be held constant relative to the balloon while the two end portions foreshorten towards the intermediate portion due to the "dog-bone" effect of the balloon. Any conventional means can be used to produce the frame 602 with reduced thickness at the end portions 610, 612, such as sanding down the end portions with sand paper or the like. In one embodiment, the end portions 610, 614 of the frame have a thickness of about 0.37 mm while the intermediate portion 614 has a thickness of about 0.45 mm.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

We claim:

1. An assembly for implanting a prosthetic heart valve in a patient's body comprising:
    a delivery apparatus comprising an elongated shaft; and
    a radially expandable prosthetic heart valve adapted to be mounted on the shaft in a radially collapsed configuration for delivery into the body, the prosthetic heart valve comprising an annular frame having an inflow end portion defining an inflow end of the frame that is configured to receive antegrade blood flow into the prosthetic heart valve when implanted, and the annular frame also having an outflow end portion defining an outflow end of the frame opposite the inflow end of the frame, the prosthetic heart valve also comprising a leaflet structure positioned within the frame, an inner fabric skirt positioned along an inner surface of the frame, and an outer fabric skirt extending from the inflow end of the frame along an outer surface of the frame to a frame attachment location;
    wherein the frame is adapted to shorten axially during radial expansion of the prosthetic valve, thereby increasing axial slack in the outer fabric skirt; and
    wherein the outer fabric skirt comprises an edge defining a plurality of alternating projections and notches that is attached to the frame at the frame attachment location.

2. The assembly of claim 1, wherein an outer diameter of the inflow end portion of the frame is smaller than an outer diameter of the outflow end portion of the frame.

3. The assembly of claim 1, wherein the leaflet structure comprises a plurality of leaflets, wherein each of the leaflets comprises:
    opposing side tabs on opposite sides of the leaflet, the side tabs being secured to the outflow end portion of the frame;
    a free outflow edge portion extending between the side tabs adjacent to the outflow end of the frame; and
    an inflow edge portion extending between the side tabs adjacent to the inflow end of the frame, the inflow edge portion comprising opposing axial edge portions that extend from the side tabs toward the inflow end of the frame in a generally axial direction and an intermediate edge portion that extends between the axial edge portions, the intermediate edge portion comprising a curved apex portion adjacent to the inflow end of the frame and a pair of oblique portions that extend between the axial edge portions and the apex portion, the oblique portions having a greater radius of curvature than the apex portion.

4. The assembly of claim 1, wherein the frame comprises three angularly spaced commissure windows each comprising an enclosed opening between first and second axially oriented side struts; and
    the leaflet structure comprises a plurality of leaflets each comprising two opposing side tabs, each side tab being paired with an adjacent side tab of an adjacent leaflet to form commissures of the leaflet structure, and wherein each commissure extends radially outwardly through a corresponding commissure window of the frame to a location outside of the frame and is sutured to the side struts of the commissure window.

5. The assembly of claim 4, wherein the commissure windows of the frame are depressed radially inwardly relative to the portions of the frame extending between adjacent commissure windows when the prosthetic valve is in the radially collapsed configuration on the shaft.

6. The assembly of claim 1, wherein the frame comprises an inflow row of openings at the inflow end portion of the frame, an outflow row of openings at the outflow end portion of the frame, and at least one intermediate row of openings between the inflow row of openings and the outflow row of openings;
    wherein the openings of the inflow row of openings are larger than the openings of the at least one intermediate row of openings.

7. The assembly of claim 1, wherein the frame has a plurality of openings and portions of the leaflet structure protrude through the openings while the prosthetic valve is in the radially collapsed configuration.

8. The assembly of claim 1, wherein the inflow end portion of the frame comprises a frame thickness that is less than a frame thickness of an intermediate portion of the frame between the inflow end portion and the outflow end portion.

9. The valve of claim 1, wherein the outer fabric skirt extends from the inflow end of the frame along the outer surface of the frame to a plurality of outer skirt attachment locations on the outer surface of frame, and wherein distances from the inflow end of the frame to the plurality of outer skirt attachment locations become smaller when the prosthetic heart valve is radially expanded.

10. The valve of claim 9, wherein when the prosthetic heart valve is radially expanded, the plurality of outer skirt attachment locations and the inflow end of the frame are at substantially the same radial distance from a longitudinal center axis of the prosthetic heart valve.

11. The valve of claim 1, wherein the projections at the edge of the outer skirt are attached to the frame and the notches in the edge of the outer skirt are not attached to the frame.

12. An assembly for implanting a prosthetic heart valve in a patient's body comprising:
    a delivery apparatus comprising an elongated shaft;
    a radially expandable and collapsible prosthetic heart valve mounted on the shaft in a radially collapsed configuration for delivery into the body, the prosthetic heart valve comprising an annular frame and a leaflet structure within the frame;
    wherein the frame comprises a plurality of angularly spaced commissure windows each comprising an enclosed opening between first and second axially oriented side struts, and the frame further comprises intermediate side struts that are axially oriented and positioned angularly between the commissure windows, and the leaflet structure comprises a plurality of commissure portions that extend outwardly through respective commissure windows to locations outside of the frame; and
    wherein the commissure windows are depressed radially inwardly relative to the intermediate side struts when the prosthetic heart valve is radially collapsed on the shaft, such that an outermost surface of each commissure portion of the leaflet structure outside of the frame is at substantially the same radial distance from a longitudinal center axis of the prosthetic heart valve as outer surfaces of the intermediate side struts.

13. The valve of claim 12, wherein the commissure windows of the frame are depressed inwardly a radial distance of between 0.2 mm and 1.0 mm relative to the intermediate side struts when the valve is radially collapsed.

14. The valve of claim 12, wherein an outer diameter of an inflow end portion of the frame is smaller than an outer diameter of an outflow end portion of the frame when the valve is radially collapsed on the shaft.

15. The assembly of claim 12, wherein an outer surface of the frame defines radial depressions in regions proximate the commissure windows, and outer portions of the commissure portions of the leaflet structure are located in the radial depressions along the outside of the frame.

16. The assembly of claim 12, wherein the commissure portions of the leaflet structure are sutured to the axially oriented side struts of the commissure windows.

17. An implantable prosthetic valve that is radially collapsible to a collapsed configuration and radially expandable to an expanded configuration, the prosthetic valve comprising:
an annular frame having a longitudinal axis extending between an inflow end of the frame and an outflow end of the frame and defining an axial direction, the inflow end of the frame being configured to receive antegrade blood flow into the prosthetic valve when implanted;
a leaflet structure positioned within the frame; and
an annular outer skirt positioned around an outer surface of the frame, the outer skirt comprising an inflow edge positioned at a first location at the inflow end of the frame, an outflow edge defining a plurality of spaced apart axial projections that are secured to the frame at a second location axially spaced from the inflow edge, and an intermediate portion extending between the inflow edge and the outflow edge and positioned outside of the frame;
wherein when the valve is in the expanded configuration, the intermediate portion of the outer skirt comprises slack in the axial direction between the inflow edge of the outer skirt and the outflow edge of the outer skirt, and when the valve is collapsed to the collapsed configuration, the distance between the inflow edge of the outer skirt and the outflow edge of the outer skirt increases, reducing the slack in the outer skirt in the axial direction.

18. The valve of claim 17, wherein the outflow edge of the outer skirt comprises a plurality of alternating projections and notches, the projections being secured to the frame at the second location, the outer skirt being unsecured to the frame at the notches.

19. The valve of claim 17, wherein the outer skirt is not stretched in the axial direction when the valve is radially collapsed to the collapsed configuration and slack is removed from the intermediate portion of the outer skirt.

20. An implantable prosthetic valve comprising:
an annular frame comprising a plurality of leaflet attachment portions; and
a leaflet structure positioned within the frame and secured to the leaflet attachment portions of the frame, the leaflet structure comprising a plurality of leaflets, each leaflet comprising a body portion having a free outflow edge, two opposing primary side tabs extending from opposite sides of the body portion, and two opposing secondary tabs, each secondary tab extending from the body portion adjacent to a respective primary side tab, the secondary tabs extending from the body portion at opposite ends of the free outflow edge;
wherein the secondary tabs are folded about radially extending creases that extend radially from the opposite ends of the free outflow edge, such that a first portion of the secondary tabs lies flat against the body portion of the respective leaflet, and the secondary tabs are folded about axially extending creases such that a second portion of the secondary tabs extends in a different plane than the first portion, wherein the radially extending creases and the axially extending creases are non-parallel.

21. The valve of claim 20, wherein the second portion of each secondary tab is sutured to a respective primary tab.

22. The valve of claim 20, wherein the secondary tabs are positioned inside of the frame.

23. The valve of claim 20, wherein the first portion of each the secondary tab pivots about the axially extending crease and lays flat against the second portion of the secondary tab when the valve is collapsed to a radially collapsed configuration.

24. The valve of claim 20, wherein the first portion of each secondary tab extends radially inwardly from the frame and comprises an inner edge spaced radially from an inner surface of the frame, and the body portion of the leaflet articulates about the inner edges of the two secondary tabs of the leaflet in response to blood flowing through the valve when the valve is in operation within a patient's body.

25. The valve of claim 20, wherein the plurality of leaflet attachment portions comprises window frame portions each comprising an enclosed opening between first and second axially oriented side struts, and wherein the primary side tabs extend radially outwardly through respective window frame portions to a location outside of the frame and are sutured to the secondary tabs to secure the leaflets around the side struts.

* * * * *